(12) United States Patent
Huang

(10) Patent No.: US 8,410,161 B2
(45) Date of Patent: Apr. 2, 2013

(54) THIOXANTHONE RING SYSTEM DERIVATIVES

(75) Inventor: Hsu-Shan Huang, Taipei (TW)

(73) Assignee: National Defense Medical Center, Taipei (TW)

( * ) Notice: Subject to any disclaimer, the term of this patent is extended or adjusted under 35 U.S.C. 154(b) by 169 days.

(21) Appl. No.: 13/154,139

(22) Filed: Jun. 6, 2011

(65) Prior Publication Data
US 2012/0088810 A1 Apr. 12, 2012

(30) Foreign Application Priority Data
Oct. 6, 2010 (TW) ................................ 99134049 A

(51) Int. Cl.
*A61K 31/382* (2006.01)
*C07D 335/16* (2006.01)
(52) U.S. Cl. .......................... 514/437; 549/27
(58) Field of Classification Search .................. 514/437; 549/27
See application file for complete search history.

(56) References Cited

U.S. PATENT DOCUMENTS
5,432,049 A * 7/1995 Fischer et al. ................. 430/342

* cited by examiner

Primary Examiner — Taofiq A Solola
(74) Attorney, Agent, or Firm — WPAT, P.C.; Anthony King

(57) ABSTRACT

A thioxanthone ring system derivative compound is provided. The thioxanthone ring system derivative compound is represented by a formula (I):

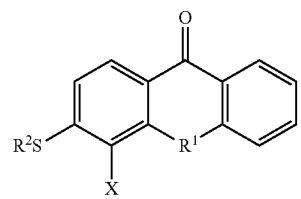

wherein X is a substituent being one selected from a group consisting of halogens, wherein $R^1$ is a substituent being one selected from a group consisting of sulfur and sulfur dioxide, wherein $R^2$ is a substituent being one selected from a group consisting of $C_1$~$C_{10}$ alkyl group, $C_3$~$C_{10}$ branched alkyl group, $C_3$~$C_{10}$ cyclic alkyl group, phenyl group, phenyl alkyl group, and wherein hydrogen of phenyl group can be partially substituted by halogens, alkoxyl group, $C_1$~$C_{10}$ alkyl group, nitro group or amine group.

15 Claims, 6 Drawing Sheets

THIOXANTHONE RING SYSTEM DERIVATIVES

CROSS-REFERENCE TO RELATED APPLICATIONS

This Non-provisional application claims priority under 35 U.S.C. §119(a) on Patent Application No(s). 099134049 filed in Taiwan, Republic of China, Oct. 6, 2010 the entire contents of which are hereby incorporated by reference.

BACKGROUND OF THE INVENTION

1. Field of the Invention

This invention relates to a pharmaceutical for treating cancer and, more particularly, to a plurality of thioxanthone ring system derivatives and pharmaceutical composition comprising the same.

2. Description of the Related Art

The main reasons of cancer are due to the unusual pathological changes of cells or unnormal proliferation. The tumor means the cell aggregated to form the phyma. There are two types of tumors: benign tumors and malignant tumors. Generally, the growing rate of benign tumors is slower and the tumors will not affect the neighbor normal tissue as well as it is not lethality. Most of them can be excised by surgery unless they grow on a vital part and relapse. Malignant tumors are generally called cancer, and the proliferation of cancer cell will invade peripheral tissues, moreover, the proliferation of cancer cell will transfer through Circulatory System or Lymphatic system. The tumor comprises solid tumor and non-solid tumor. The cancer caused by the solid tumor comprises lung cancer, colorectal cancer, central nervous system cancer, melanoma, ovarian cancer, prostate cancer, kidney cancer, breast cancer, small cell cervical cancer, gastric cancer, cervical cancer, osteosarcoma . . . etc. The cancer caused by the non-solid tumor comprises is Leukemia, lymphoma cancer, multiple myeloma . . . etc.

Generally, the method for treating cancer can be separated into three kinds: surgery, radiation therapy and chemotherapy. And then, the appropriate method is decided upon the position of tumor and the status of the patient. In recent years, some new methods for treating cancer cell are disclosed, for example, gene therapy, molecular targeted therapies, antigenic therapy.

In recent years, the medical research finds that chronic inflammation will result in a chronic disease, such as cancer, diabetes mellitus . . . etc. Therefore, it points out that anthraquinone derivatives such as spiro-thioxanthene and spiro-xanthene-9,2-[1,3,4]-thiadiazole can inhibit human's inflammation (H. N. Hafez et al. Bioorganic & Medicinal Chemistry Letters, 2008, 18). Furthermore, it also points out anthraquinone derivatives such as 6-[[(Diphenylmethylene) amino]oxy]hexanoic Acid can cure Diabetes mellitus (D. Rakowitz et al. Arch. Pharm. Chem. Life Sci. 2007).

In addition, duplicating and maintaining the length of the telomere, which is located at the end of a chromosome, must rely on telomerase. A lot of research points out that the telomerase activity is rarely detected in normal human somatic cells, but is usually detected in the cells that keep proliferating, such as hematopoietic cells, embryogenic cells, stem cells, germ cell, immortalized cell, tumor cells, etc. Therefore, in normal somatic cells, the telomere gets shortened at each time of cell mitosis. When the telomere is shortened to some level, the cell will lose the ability of replication and go into apoptosis stage, and this stage is also called M1 stage (mortality stage 1).

In the M1 stage, tumor suppressor gene of the cells mutate as p53 and Rb to make the cells leave the M1 stage and keep processing cell mitosis. The above situation is called M2 stage (mortality stage 2). In M2 stage, the telomerase activity doesn't exist so that the length of the telomere will shorten to result in the instability of the chromosome. Therefore, the signal transduction of the cells cannot perform result in the death of the cells. According to the abovementioned, the M2 stage is also called crisis, and most cells will died during the M2 stage. However, few cells will survive due to the telomerase activity, and the few cells will keep processing the cell mitosis to turn into the immortalized cells or the tumor cells.

Because the telomerase activity is rarely detected in normal human somatic cells, but is usually detected in the tumor cells so that the telomerase becomes the newly objective of the related research about the target therapy.

In some cells, which quickly proliferate and grow, its supercoiled structure needs to be entangled and disentangled for processing DNA transcription and translation so that topoisomerase, which is responsible for the abovementioned actions, is a newly objective for target therapy. The abovementioned objective is used to maintain a break portion while DNA disentangles for inhibiting the cancer cells. The inhibition mechanism of the topoisomerase has three types illustrated as follows. The first type is that drugs combines with DNA fragment, and then the topoisomerase II combines with the complex formed by the drugs and DNA. The second type is that the topoisomerase II combines with DNA fragment first, and then the drugs combines with the complex formed by the topoisomerase II and DNA. The last type is that the drugs will combines with the topoisomerase II, and then the complex formed by the drugs and the topoisomerase II will combines with the DNA fragment. To sum up the above three types, ternary complex including the topoisomerase, the drugs and the DNA fragment will be formed. The main mechanism of the abovementioned action is that DNA stands are first broken by the topoisomerase. And then, the complex composed of the topoisomerase and the drugs will fix on the DNA. Because the broken DNA cannot combine again so that the enzyme cannot act. Therefore, it will be determined that DNA is broken to result in the death of the cells. Some anti-cancer drugs, such as doxorubicin and mitoxantrone, reach the good effect for curing cancer by inhibiting the topoisomerase.

BRIEF SUMMARY OF THE INVENTION

In accordance with the first aspect of the present invention, a thioxanthone ring system derivative compound is provided. The compound is represented by a formula (I):

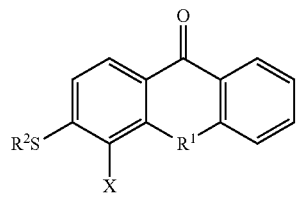

wherein X is a substituent being one selected from a group consisting of halogens, wherein $R^1$ is a substituent being one selected from a group consisting of sulfur and sulfur dioxide, wherein R² is a substituent being one selected from a group consisting of C₁~C₁₀ alkyl group, C₃~C₁₀ branched alkyl group, C₃~C₁₀ cyclic alkyl group, phenyl group, phenyl alkyl group, and wherein hydrogen of phenyl group being partially substituted by halogens, alkoxyl group, C₁~C₁₀ alkyl group, nitro group or amine group.

Preferably, R² is C₁~C₁₀ alkyl group, and one selected from a group consisting of a methyl group, an ethyl group, a propyl group, a butyl group, a pentyl group, a hexyl group, a heptyl group, an octyl group, an nonyl group and a decyl group.

Preferably, R² is an ethyl group or a propyl group.

Preferably, R² is C₃~C₁₀ branched alkyl group, and one selected from a group consisting of an isobutyl group, an isopentyl group, 2-methylbutyl group, 2-methylpentyl group, 3-methylpentyl group, 2-methylhexyl group, 3-methylhexyl group, 2-ethylpentyl group, 2-methylheptyl group, 3-methylheptyl group, 4-methylheptyl group, 3-ethylpentyl group, 2-methyloctyl group, 3-methyloctyl group, 4-methyloctyl group, 3-ethylheptyl group, 4-ethylheptyl group, 2-methylnonyl group, 3-methylnonyl group, 4-methylnonyl group, 5-methylnonyl group, 3-ethyloctyl group, 4-ethyloctyl group.

Preferably, R² is an isobutyl group.

Preferably, R² is C₃~C₁₀ cyclic alkyl group, and one selected from a group consisting of a cyclopropyl group, a cyclobutyl group, a cyclopentyl group, a cyclohexyl group, a cycloheptyl group, a cyclooctyl group, a cyclononyl group, a cyclodecyl group.

Preferably, R² is a cyclopentyl group.

Preferably, R² is a phenyl group or a phenyl alkyl group, and one selected from a group consisting of a nitrophenyl group, an alkoxyphenyl group, an aminophenyl group, a methylphenyl group, a chlorophenyl group, a bromophenyl group, an isopropylphenyl group, an ethylphenyl group.

Preferably, R² is a 4-nitrophenyl group, a 2-methoxyphenyl group, a 3-methoxyphenyl group, a 4-methoxyphenyl group, a 2-ethoxyphenyl group, a 2-aminophenyl group, a 3-aminophenyl group, a 2-methylphenyl group, a 3-methylphenyl group, a 4-methylphenyl group, a 3-chlorophenyl group, a 4-chlorophenyl group, a 2,3-dichlorophenyl group, a 4-bromophenyl group, a 2,4-dimethylphenyl group, a 2,5-dimethylphenyl group, a 2,6-dimethylphenyl group, a 3,4-dimethylphenyl group, a 3,5-dimethylphenyl group, a 2-isopropylphenyl group, a 4-isopropyl group or a 2-ethylphenyl group.

Preferably, R² is a 2-chlorophenylmethyl group, a 4-fluorophenylmethyl group, a 4-bromophenylmethyl group, a 4-chlorophenylmethyl group, a 4-methoxyphenylmethyl group, a 2,4,6-trimethylphenyl group or a 4-isopropylphenylmethyl group.

Preferably, halogen is one selected from a group consisting of a fluorine, a chlorine, a bromine and an iodine.

In accordance with the second aspect of the present invention, a pharmaceutical composition for inhibiting tumor growth is provided. The pharmaceutical composition comprises a thioxanthone ring system derivative compound with an effective amount and a pharmaceutically acceptable excipient, wherein the thioxanthone ring system derivative compound is represented by a formula (I):

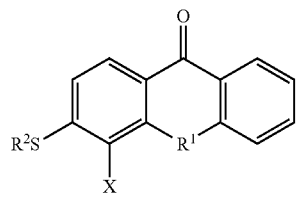

Preferably, tumor is a solid tumor or a no-solid tumor.

Preferably, a cancer having the solid tumor comprises lung cancer, colorectal cancer, central nervous system cancer, melanoma, ovarian cancer, prostate cancer, kidney cancer, breast cancer.

Preferably, a cancer having the non-solid tumor is Leukemia.

This invention will process pharmacological activity assay of the thioxanthone ring system derivative compound, and evaluate the effect of inhibiting telomerase activity, inhibiting topoisomerase activity, inhibiting tumor growth and treating cancer with a series embodiments as follows.

DETAILED DESCRIPTION OF THE INVENTION

Figure 1:
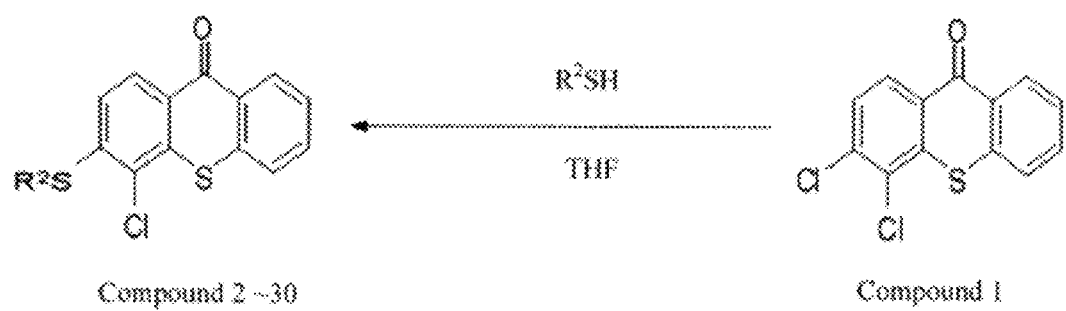
FIG. 1 is a flow chart for manufacturing the compound No. 2~30.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

The present invention provides a serious of thioxanthone ring system derivative compound, and further provides a method for manufacturing the same and a pharmaceutical composition comprising the same. The thioxanthone ring system derivative compound is represented by a formula (I):

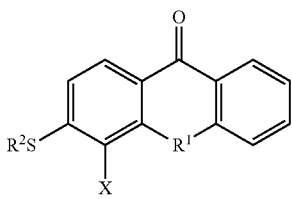

wherein X represents halogens, and may be one selected from a group consisting of a fluorine, a chlorine, a bromine and an iodine. Preferably, halogen is the chlorine due to its larger electronegativity for increasing the electropositivity of the thioxanthone.

In the formula (I), $R^1$ is a substituent being one selected from a group consisting of sulfur and sulfur dioxide. A substituent group of the side chain is mainly mercaptan for being comparable with the sulfur in its three-ring structure and the bonding of DNA. The thiophenol group is more preferred because the sulfur in the three-ring structure is a planar structure and chelated by the two benzene rings, however, the benzene ring combined with the sulfur of the thiophenol group can rotate free for increasing the combination effect between the side chain and DNA.

Therefore, $R^2$ is a substituent being one selected from a group consisting of $C_1$~$C_{10}$ alkyl group, $C_3$~$C_{10}$ branched alkyl group, $C_3$~$C_{10}$ cyclic alkyl group, phenyl group, phenyl alkyl group, and wherein hydrogen of phenyl group being partially substituted by halogens, alkoxyl group, $C_1$~$C_{10}$ alkyl group, nitro group or amine group.

In a preferred embodiment, $R^2$ can be a substituent being one selected from a group consisting of an ethyl group, a propyl group, an isopropyl group, a cyclopentyl group, a 4-nitrophenyl group, a 2-methoxyphenyl group, a 3-methoxyphenyl group, a 4-methoxyphenyl group, a 2-ethoxyphenyl group, a 2-aminophenyl group, a 3-aminophenyl group, a 2-methylphenyl group, a 3-methylphenyl group, a 4-methylphenyl group, a 3-chlorophenyl group, a 4-chlorophenyl group, a 2,3-dichlorophenyl group, a 4-bromophenyl group, a 2,4-dimethylphenyl group, a 2,5-dimethylphenyl group, a 2,6-dimethylphenyl group, a 3,4-dimethylphenyl group, a 3,5-dimethylphenyl group, a 2-isopropylphenyl group, a 4-isopropyl group, a 2-ethylphenyl group, a 2-chlorophenylmethyl group, a 4-fluorophenylmethyl group, a 4-bromophenylmethyl group, a 4-chlorophenylmethyl group, a 4-methoxyphenylmethyl group, a 2,4,6-trimethylphenyl group or a 4-isopropylphenylmethyl group.

The following process provides a method for manufacturing the thioxanthone ring compound. The steps are examples, as is the sequence, steps maybe added, removed, or copeated.

Please refer to FIG. 1, the mercaptan solution with a $R^2$ substituent ($R^2$SH, 2 mmol) is dropped in 10 ml of methanol contained sodium methoxide (0.108 g, 2 mmol) to form a first solution. After stirring for 15 minutes, 10 ml of tetrahydrofuran solution contained 3,4-dichloro-9H-thioxanthen-9-one (No. 1, 0.28 g, 1 mmol) is added thereinto to obtain a second solution. The second solution is then treated by a reverse flow under 120° C. for 2 hours and left to cool down to the room temperature. After filtering the mixture, the filtrate (the third solution) is dried by using a rotary evaporator to obtain a precipitate, and then removed impurities from the precipitate by dichloromethane. After filtering once more and washing by ethanol, a series of the thioxanthone ring system derivatives are obtained, that is, the compound No. 2~30.

Figure 2:
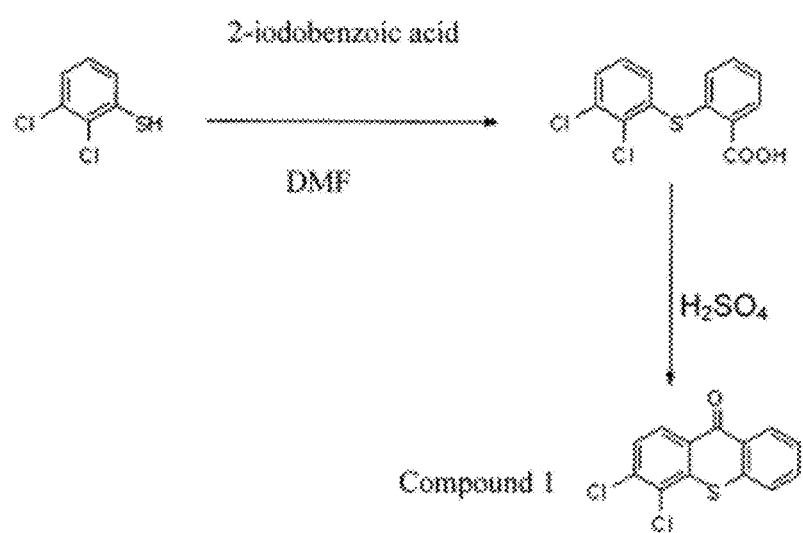
FIG. 2 is a flow chart for manufacturing the compound No. 1.

FIG. 2 is a flow chart for manufacturing the compound No. 1. First, 2,3-dichlorobenzenethiol (0.90 g, 5 mmol) is dissolved in 10 ml DMF solution, and 10 ml of 1N $KOH_{(aq)}$ is added thereinto. After stirring the mixture under room temperature for 10~15 minutes, 2-iodobenzoic acid (1.24 g, 5 mmol) is dissolved in 10 ml of DMF solution. And then, 0.315 g of Cupper powder is added into the mixture, and the mixture is treated by a reverse flow under 120□ for 8 hours. After filtering the mixture, the filtrate is neutralized with 10 ml of 1N $HCl_{(aq)}$, and a precipitate will be produced. After filtering and washing the precipitate by water, 2-(2,3-dichlorophenylthio)benzoic acid is obtained.

And then, 2-(2,3-dichlorophenylthio)benzoic acid (0.75 g, 2.5 mmol) is added into 75% $H_2SO_{4(aq)}$, and stirred under 110° C. for 4~6 hours by using an oil bath. After the turbid solution changes to the clear and sticky solution, the mixture is transferred into 200 mL of icy water. After filtering, the precipitate is collected. The precipitate is then extracted several times by $CH_2Cl_2$ and dried by $MgSO_4$, so as to obtain the compound No. 1 (3,4-dichloro-9H-thioxanthen-9-one).

According to the abovementioned compound No. 1, the method for manufacturing a plurality of the thioxanthone ring system derivatives by using the compound No. 1 as the reactant in the beginning and the analytic results about them will be disclosed with a series embodiments as follows.

Embodiment 1 (4-Chloro-3-(ethylthio)-9H-thioxanthen-9-one, No. 2)

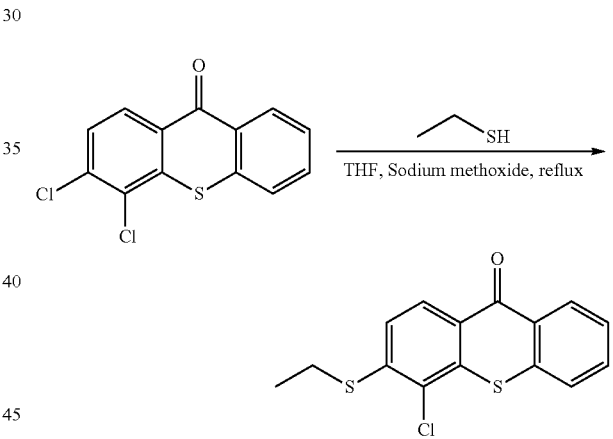

Ethanethiol (2 mmol) with appropriate amount is slowly dropped into 10 mL of methanol contained sodium methoxide (0.108 g, 2 mmol). The abovementioned solution is stirred under room temperature, and 10 mL of tetrahydrofuran solution contained the compound No. 1 (0.28 g, 1 mmol) is slowly dropped thereinto. The mixture is then treated by a reverse flow under 120° C. for 2 hours and left to cool down to the room temperature. After filtering the mixture, the filtrate is dried by using a rotary evaporator and then removed impurities by dichloromethane. After filtering once more, the precipitate is collected and washed by ethanol, so as to obtain the yellow compound No. 2.

The compound No. 2 has the following characteristics: Mol. Wt.: 306.8302 ($C_{15}H_{11}ClOS_2$); $R_f$: 0.45 (ethyl acetate: n-hexane=1:6); Yield: 36%; Mp.: 207-208° C. (ethanol); HRMS (EI) m/z: calcd, 305.9940 $[M]^+$; found, 305.9932; 1H-NMR (300 MHz, DMSO-$d_6$) δ (ppm): 1.46 (t, J=7.5 Hz, 3H, —$CH_3$), 3.11 (q, J=7.5 Hz, 2H, —$CH_2$—), 7.33 (d, J=8.7 Hz, 1H, Ar—$H_2$), 7.48-7.54 (m, 1H, Ar—$H_6$), 7.62-7.66 (m, 2H, Ar—$H_{57}$), 8.52 (d, J=8.7 Hz, 1H, Ar—$H_1$), 8.59 (dt, J=8.7

Hz, J=0.9 Hz, 1H, Ar—H$_8$); 13C-NMR (300 MHz, CDCl$_3$) δ (ppm): 13.45, 25.93, 122.57, 126.59, 126.88, 127.57, 128.35, 128.60, 129.85, 132.61, 136.86, 144.33, 179.62 (CO).

Embodiment 2 (4-Chloro-3-(propylthio)-9H-thioxanthen-9-one, No. 3)

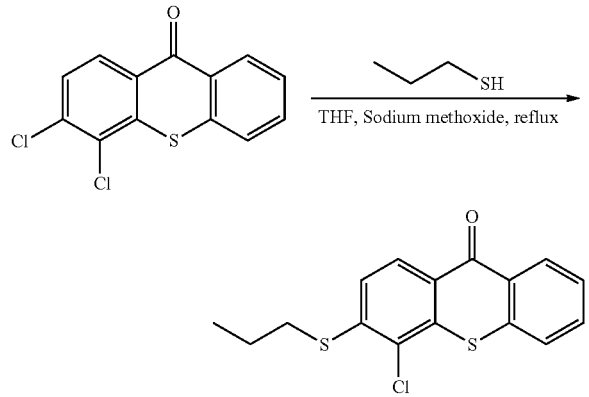

1-Propanethiol (2 mmol) with appropriate amount is slowly dropped into 10 mL of methanol contained sodium methoxide (0.108 g, 2 mmol). The abovementioned solution is stirred under room temperature, and 10 mL of tetrahydrofuran solution contained the compound No. 1 (0.28 g, 1 mmol) is slowly dropped thereinto. The mixture is then treated by a reverse flow under 120☐ for 2 hours and left to cool down to the room temperature. After filtering the mixture, the filtrate is dried by using a rotary evaporator and then removed impurities by dichloromethane. After filtering once more, the precipitate is collected and washed by ethanol, so as to obtain the white compound No. 3.

The compound No. 3 has the following characteristics: Mol. Wt.: 320.8568 (C$_{16}$H$_{13}$ClOS$_2$); R$_f$: 0.55 (ethyl acetate: n-hexane=1:6); Yield: 45%; Mp.: 240-242° C. (ethanol); HRMS (EI) m/z: calcd, 320.0096 [M]$^+$; found, 320.0096; 1H-NMR (300 MHz, CDCl$_3$) δ(ppm): 1.13 (t, J=7.2 Hz, 3H, —CH$_3$), 1.82 (q, J=7.2 Hz, 2H, —CH$_2$—), 3.05 (t, J=7.2 Hz, 2H, —CH$_2$—), 7.32 (d, J=8.7 Hz, 1H, Ar—H$_2$), 7.45-7.53 (m, 1H, Ar—H$_6$), 7.62-7.66 (m, 1H, Ar—H$_{5,7}$), 8.51 (d, J=8.7 Hz, 1H, Ar—H$_1$), 8.57 (dt, J=8.1 Hz, J=0.9 Hz, 1H, Ar—H$_8$); 13C-NMR (300 MHz, CDCl$_3$) δ (ppm): 13.43, 21.84, 33.77, 115.56, 122.54, 126.58, 126.86, 127.41, 128.29, 128.52, 129.81, 132.61, 136.83, 137.50, 144.53, 179.61 (CO).

Embodiment 3 (4-Chloro-3-(isopropylthio)-9H-thioxanthen-9-one, No. 4)

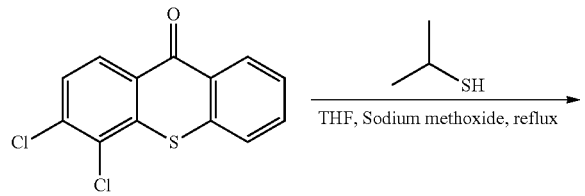

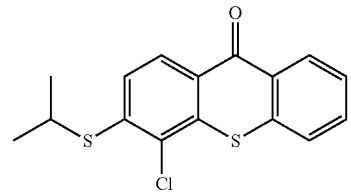

2-isopropanethiol (2 mmol) with appropriate amount is slowly dropped into 10 mL of methanol contained sodium methoxide (0.108 g, 2 mmol). The abovementioned solution is stirred under room temperature, and 10 mL of tetrahydrofuran solution contained the compound No. 1 (0.28 g, 1 mmol) is slowly dropped thereinto. The mixture is then treated by a reverse flow under 120☐ for 2 hours and left to cool down to the room temperature. After filtering the mixture, the filtrate is dried by using a rotary evaporator and then removed impurities by dichloromethane. After filtering once more, the precipitate is collected and washed by ethanol, so as to obtain the ivory compound No. 4.

The compound No. 4 has the following characteristics: Mol. Wt.: 320.8568 (C$_{16}$H$_{13}$ClOS$_2$); R$_f$: 0.37 (ethyl acetate: n-hexane=1:6); Yield: 42%; Mp.: 161-162° C. (ethanol); HRMS (EI) m/z: calcd, 320.0096 [M]$^+$; found, 320.0089; 1H-NMR (300 MHz, CDCl$_3$) δ(ppm): 1.46 (d, J=6.6 Hz, 6H, —CH$_3$), 3.69 (q, J=6.6 Hz, 1H, —CH—), 7.39 (d, J=9.0 Hz, 2H, Ar—H$_2$), 7.48-7.53 (m, 1H, Ar—H$_6$), 7.62-7.66 (m, 2H, Ar—H$_{5,7}$), 8.51 (d, J=9.0 Hz, 1H, Ar—H$_1$), 8.57 (dt, J=8.1 Hz, J=0.9 Hz, 1H, Ar—H$_8$); 13C-NMR (300 MHz, CDCl$_3$) δ (ppm): 22.77, 29.61, 36.16, 124.17, 126.59, 126.88, 127.72, 128.24, 128.50, 129.81, 132.63, 136.90, 137.70, 143.75, 179.63 (CO).

Embodiment 4 (4-Chloro-3-(cyclopentylthio)-9H-thioxanthen-9-one, No. 5)

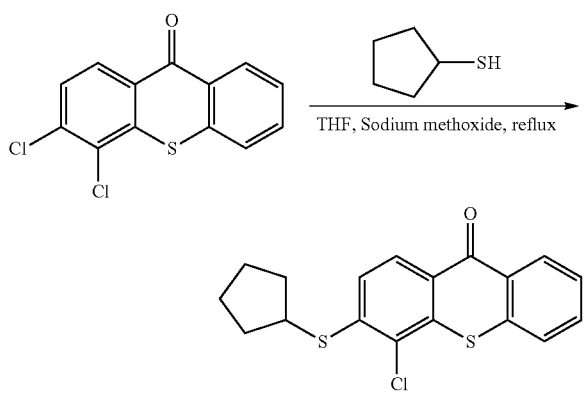

Cyclopentanethiol (2 mmol) with appropriate amount is slowly dropped into 10 mL of methanol contained sodium methoxide (0.108 g, 2 mmol). The abovementioned solution is stirred under room temperature, and 10 mL of tetrahydrofuran solution contained the compound No. 1 (0.28 g, 1 mmol) is slowly dropped thereinto. The mixture is then treated by a reverse flow under 120☐ for 2 hours and left to cool down to the room temperature. After filtering the mixture, the filtrate is dried by using a rotary evaporator and then removed impurities by dichloromethane. After filtering once more, the precipitate is collected and washed by ethanol, so as to obtain the white compound No. 5.

The compound No. 5 has the following characteristics: Mol. Wt.: 346.8941 ($C_{18}H_{15}ClOS_2$); $R_f$: 0.63 (ethyl acetate: n-hexane=1:6); Yield: 57%; Mp.: 209-210° C. (ethanol); HRMS (EI) m/z: calcd, 346.0253 $[M]^+$; found, 346.0246; 1H-NMR (300 MHz, $CDCl_3$) δ(ppm): 1.66-1.86 (m, 6H, —$CH_2$—), 2.19-2.28 (m, 2H, —$CH_2$—), 3.80 (m, 1H, —CH—), 7.41 (d, J=7.8 Hz, 1H, Ar—$H_2$), 7.48-7.53 (m, 1H, Ar—$H_6$), 7.62-7.66 (m, 2H, Ar—$H_{5,7}$), 8.51 (d, J=7.8 Hz, 1H, Ar—$H_1$), 8.57 (dt, J=8.4 Hz, J=0.9 Hz, 1H, Ar—$H_8$); 13C-NMR (300 MHz, $CDCl_3$) δ(ppm): 25.02, 33.52, 43.97, 123.75, 126.59, 126.85, 127.46, 128.22, 128.60, 129.82, 132.57, 136.90, 137.50, 145.22, 179.64 (CO).

Embodiment 5 (4-Chloro-3-(phenylthio)-9H-thioxanthen-9-one, No. 6)

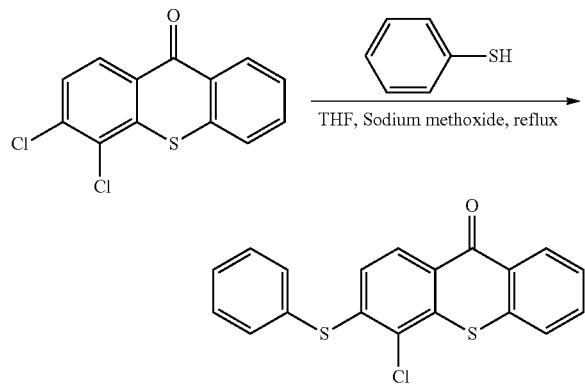

Benzenethiol (2 mmol) with appropriate amount is slowly dropped into 10 mL of methanol contained sodium methoxide (0.108 g, 2 mmol). The abovementioned solution is stirred under room temperature, and 10 mL of tetrahydrofuran solution contained the compound No. 1 (0.28 g, 1 mmol) is slowly dropped thereinto. The mixture is then treated by a reverse flow under 120☐ for 2 hours and left to cool down to the room temperature. After filtering the mixture, the filtrate is dried by using a rotary evaporator and then removed impurities by dichloromethane. After filtering once more, the precipitate is collected and washed by ethanol, so as to obtain the white compound No. 6.

The compound No. 6 has the following characteristics: Mol. Wt.: 354.8730 ($C_{19}H_{11}ClOS_2$); $R_f$: 0.52 (ethyl acetate: n-hexane=1:6); Yield: 34%; Mp.: 180-181° C. (ethanol); HRMS (EI) m/z: calcd, 353.9940 $[M]^+$; found, 353.9943; 1H-NMR (300 MHz, $CDCl_3$) δ(ppm): 6.79 (d, J=8.7 Hz, 1H, Ar—$H_2$), 7.48-7.55 (m, 4H, Ar—H), 7.58-7.63 (m, 2H, Ar—$H_7$), 7.65-7.66 (m, 2H, Ar—$H_{5,7}$), 8.32 (d, J=8.7 Hz, 1H, Ar—$H_1$), 8.55 (dt, J=7.8 Hz, J=0.9 Hz, 1H, Ar—$H_8$); 13C-NMR (300 MHz, $CDCl_3$) δ(ppm): 123.95, 126.47, 126.79, 127.85, 128.13, 128.38, 129.06, 129.68, 129.85, 129.99, 130.14, 132.48, 135.54, 136.61, 137.41, 145.15, 179.26 (CO).

Embodiment 6 (4-Chloro-3-(o-tolylthio)-9H-thioxanthen-9-one, No. 7)

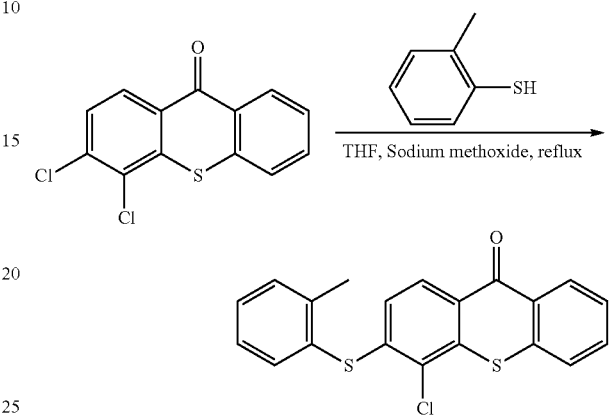

2-Methylbenzenethiol (2 mmol) with appropriate amount is slowly dropped into 10 mL of methanol contained sodium methoxide (0.108 g, 2 mmol). The abovementioned solution is stirred under room temperature, and 10 mL of tetrahydrofuran solution contained the compound No. 1 (0.28 g, 1 mmol) is slowly dropped thereinto. The mixture is then treated by a reverse flow under 120☐ for 2 hours and left to cool down to the room temperature. After filtering the mixture, the filtrate is dried by using a rotary evaporator and then removed impurities by dichloromethane. After filtering once more, the precipitate is collected and washed by ethanol, so as to obtain the white compound No. 7.

The compound No. 7 has the following characteristics: Mol. Wt.: 368.8996 ($C_{20}H_{13}ClOS_2$); $R_f$: 0.48 (ethyl acetate: n-hexane=1:6); Yield: 41%; Mp.: 208-210° C. (ethanol); HRMS (EI) m/z: calcd, 368.0096 $[M]^+$; found, 368.0092; 1H-NMR (300 MHz, $CDCl_3$) δ(ppm): 2.39 (s, 3H, —$CH_3$), 6.60 (d, J=8.7 Hz, 1H, Ar—$H_2$), 7.32 (td, J=7.2 Hz, J=2.4 Hz, 1H, Ar—H), 7.40-7.54 (m, 3H, Ar—H), 7.59-7.65 (m, 3H, Ar—H), 8.30 (d, J=8.7 Hz, 1H, Ar—$H_1$), 8.54 (dt, J=8.1 Hz, J=0.9 Hz, 1H, Ar—$H_8$); 13C-NMR (300 MHz, $CDCl_3$) δ(ppm): 20.52, 123.32, 126.59, 126.89, 127.67, 127.88, 128.30, 128.62, 128.88, 129.84, 130.81, 131.55, 132.58, 136.76, 137.12, 137.60, 143.39, 144.83, 179.50 (CO).

Embodiment 7 (4-Chloro-3-(m-tolylthio)-9H-thioxanthen-9-one, No. 8)

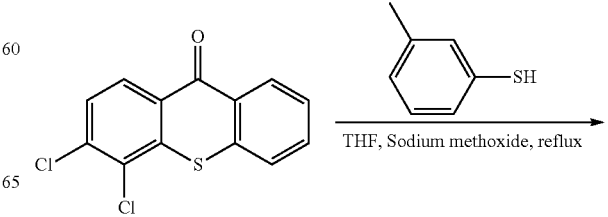

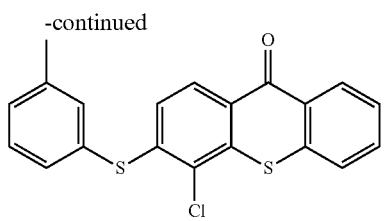

3-Methylbenzenethiol (2 mmol) with appropriate amount is slowly dropped into 10 mL of methanol contained sodium methoxide (0.108 g, 2 mmol). The abovementioned solution is stirred under room temperature, and 10 mL of tetrahydrofuran solution contained the compound No. 1 (0.28 g, 1 mmol) is slowly dropped thereinto. The mixture is then treated by a reverse flow under 120□ for 2 hours and left to cool down to the room temperature. After filtering the mixture, the filtrate is dried by using a rotary evaporator and then removed impurities by dichloromethane. After filtering once more, the precipitate is collected and washed by ethanol, so as to obtain the white compound No. 8.

The compound No. 8 has the following characteristics: Mol. Wt.: 368.8996 ($C_{20}H_{13}ClOS_2$); $R_f$: 0.46 (ethyl acetate: n-hexane=1:6); Yield: 38%; Mp.: 169-170° C. (ethanol); HRMS (EI) m/z: calcd, 368.0096 $[M]^+$; found, 368.0095; 1H-NMR (300 MHz, $CDCl_3$) δ(ppm): 2.41 (s, 3H, —$CH_3$), 6.80 (d, J=8.7 Hz, 1H, Ar—$H_2$), 7.29-7.36 (m, 1H, Ar—H), 7.38-7.42 (m, 3H, Ar—H), 7.48-7.53 (m, 1H, Ar—$H_6$), 7.63-7.66 (m, 2H, Ar—$H_{5,7}$), 8.32 (d, J=8.7 Hz, 1H, Ar—$H_1$), 8.56 (dt, J=8.1 Hz, J=0.9 Hz, 1H, Ar—$H_8$); 13C-NMR (300 MHz, $CDCl_3$) δ (ppm): 21.15, 124.15, 126.60, 126.91, 128.23, 129.84, 130.03, 130.94, 132.60, 132.65, 136.14, 136.79, 137.51, 140.32, 179.54 (CO).

Embodiment 8 (4-Chloro-3-(p-tolylthio)-9H-thioxanthen-9-one, No. 9)

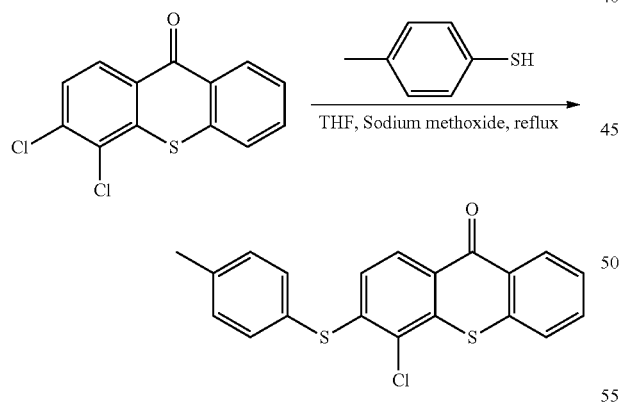

4-Methylbenzenethiol (2 mmol) with appropriate amount is slowly dropped into 10 mL of methanol contained sodium methoxide (0.108 g, 2 mmol). The abovementioned solution is stirred under room temperature, and 10 mL of tetrahydrofuran solution contained the compound No. 1 (0.28 g, 1 mmol) is slowly dropped thereinto. The mixture is then treated by a reverse flow under 120□ for 2 hours and left to cool down to the room temperature. After filtering the mixture, the filtrate is dried by using a rotary evaporator and then removed impurities by dichloromethane. After filtering once more, the precipitate is collected and washed by ethanol, so as to obtain the white compound No. 9.

The compound No. 9 has the following characteristics: Mol. Wt.: 368.8996 ($C_{20}H_{13}ClOS_2$); $R_f$: 0.46 (ethyl acetate: n-hexane=1:6); Yield: 51%; Mp.: 203-204° C. (ethanol); HRMS (EI) m/z: calcd, 368.0096 $[M]^+$; found, 368.0100; 1H-NMR (300 MHz, $CDCl_3$) δ(ppm): 2.45 (s, 3H, —$CH_3$), 6.75 (d, J=9.0 Hz, 1H, Ar—$H_2$), 7.36 (d, J=7.5 Hz, 2H, Ar—H), 7.47-7.53 (m, 3H, Ar—H), 7.64-7.66 (m, 2H, Ar—$H_{5,7}$), 8.31 (d, J=8.7 Hz, 1H, Ar—$H_1$), 8.55 (dt, J=8.1 Hz, J=0.9 Hz, 1H, Ar—$H_8$); 13C-NMR (300 MHz, $CDCl_3$) δ (ppm): 21.26, 123.72, 126.60, 126.89, 128.18, 128.53, 129.81, 131.07, 132.60, 135.87, 136.74, 140.69, 146.04, 179.55 (CO).

Embodiment 9 (4-Chloro-3-(2,4-dimethylphenylthio)-9H-thioxanthen-9-one, No. 10)

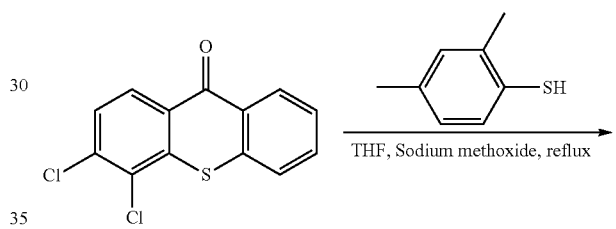

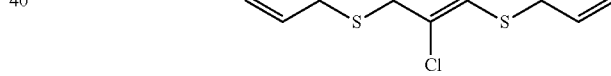

2,4-Dimethylbenzenethiol (2 mmol) with appropriate amount is slowly dropped into 10 mL of methanol contained sodium methoxide (0.108 g, 2 mmol). The abovementioned solution is stirred under room temperature, and 10 mL of tetrahydrofuran solution contained the compound No. 1 (0.28 g, 1 mmol) is slowly dropped thereinto. The mixture is then treated by a reverse flow under 120□ for 2 hours and left to cool down to the room temperature. After filtering the mixture, the filtrate is dried by using a rotary evaporator and then removed impurities by dichloromethane. After filtering once more, the precipitate is collected and washed by ethanol, so as to obtain the white compound No. 10.

The compound No. 10 has the following characteristics: Mol. Wt.: 382.9262 ($C_{21}H_{15}ClOS_2$); $R_f$: 0.53 (ethyl acetate: n-hexane 1:6); Yield: 28%; Mp.: 172-173° C. (ethanol); HRMS (EI) m/z: calcd, 382.0253 $[M]^+$; found, 382.0258; 1H-NMR (300 MHz, $CDCl_3$) δ(ppm): 2.35 (d, J=9.6 Hz, 6H, —$CH_3$), 6.61 (d, J=8.7 Hz, 1H, Ar—$H_2$), 7.30 (d, J=7.2 Hz, 1H, Ar—H), 7.43 (s, 1H, Ar—H), 7.48-7.53 (m, 1H, Ar—$H_6$), 7.65-7.66 (m, 2H, Ar—$H_{5,7}$), 8.31 (d, J=8.7 Hz, 1H, Ar—$H_1$), 8.55 (dt, 1H, J=8.1 Hz, J=0.9 Hz, Ar—$H_8$); 13C-NMR (300 MHz, CDCl$_3$) δ (ppm): 20.41, 21.15, 123.09, 125.16, 126.58, 126.86, 127.71, 128.23, 128.52, 128.62, 129.81, 132.42, 132.55, 136.77, 137.19, 137.52, 141.30, 143.26, 145.39, 179.54 (CO).

Embodiment 10 (4-Chloro-3-(2,5-dimethylphenylthio)-9H-thioxanthen-9-one, No. 11)

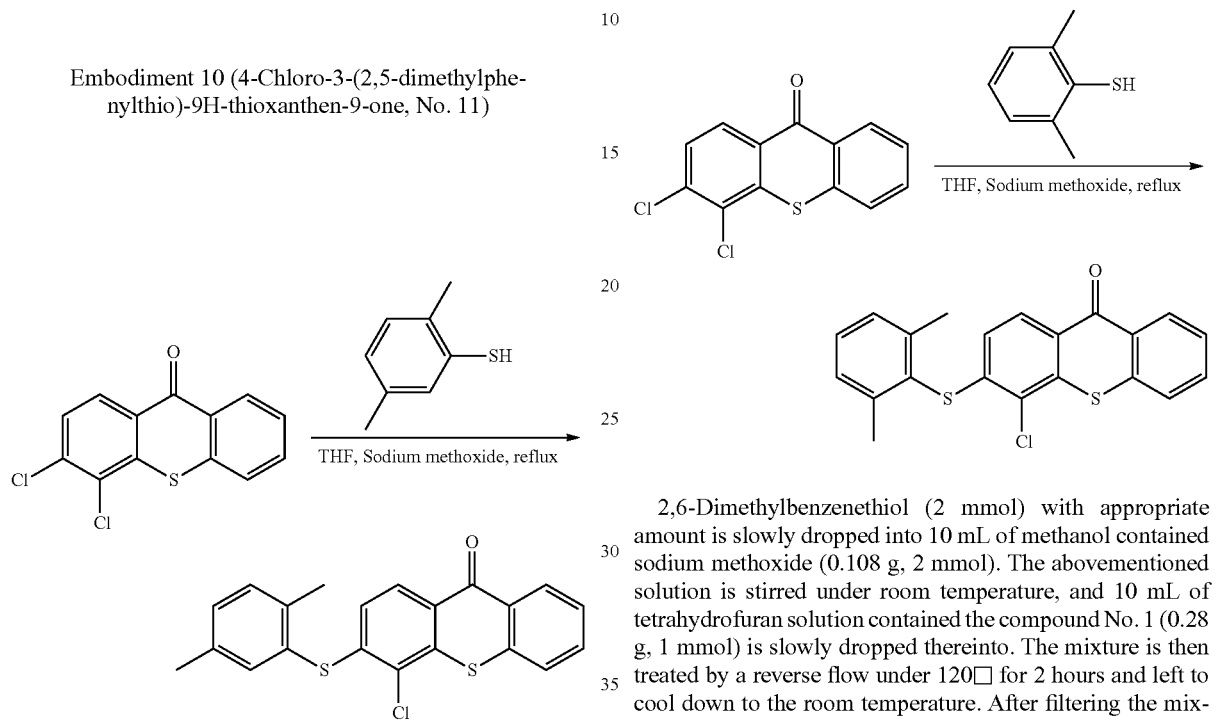

2,5-Dimethylbenzenethiol (2 mmol) with appropriate amount is slowly dropped into 10 mL of methanol contained sodium methoxide (0.108 g, 2 mmol). The abovementioned solution is stirred under room temperature, and 10 mL of tetrahydrofuran solution contained the compound No. 1 (0.28 g, 1 mmol) is slowly dropped thereinto. The mixture is then treated by a reverse flow under 120□ for 2 hours and left to cool down to the room temperature. After filtering the mixture, the filtrate is dried by using a rotary evaporator and then removed impurities by dichloromethane. After filtering once more, the precipitate is collected and washed by ethanol, so as to obtain the white compound No. 11.

The compound No. 11 has the following characteristics: Mol. Wt.: 382.9262 ($C_{21}H_{15}ClOS_2$); $R_f$: 0.47 (ethyl acetate: n-hexane=1:6); Yield: 36%; Mp.: 179-180° C. (ethanol); HRMS (EI) m/z: calcd, 382.0253 [M]$^+$; found, 382.0247; $^1$H-NMR (300 MHz, CDCl$_3$) δ(ppm): 2.35 (d, J=9.6 Hz, 6H, —CH$_3$), 6.61 (d, J=8.7 Hz, 1H, Ar—$H_2$), 7.23-7.31 (m, 2H, Ar—H), 7.42 (s, 1H, Ar—H), 7.47-7.53 (m, 1H, Ar—$H_6$), 7.64-7.66 (m, 2H, Ar—$H_{5,7}$), 8.30 (d, J=8.7 Hz, 1H, Ar—$H_1$), 8.55 (dt, J=7.5 Hz, J=0.9 Hz, Ar—$H_8$); 13C-NMR (300 MHz, CDCl$_3$) δ (ppm): 19.99, 20.59, 123.28, 126.59, 126.88, 127.75, 128.26, 128.35, 128.61, 129.83, 131.36, 131.68, 132.57, 136.77, 137.51, 137.57, 140.17, 145.13, 179.54 (CO).

Embodiment 11 (4-Chloro-3-(2,6-dimethylphenylthio)-9H-thioxanthen-9-one, No. 12)

2,6-Dimethylbenzenethiol (2 mmol) with appropriate amount is slowly dropped into 10 mL of methanol contained sodium methoxide (0.108 g, 2 mmol). The abovementioned solution is stirred under room temperature, and 10 mL of tetrahydrofuran solution contained the compound No. 1 (0.28 g, 1 mmol) is slowly dropped thereinto. The mixture is then treated by a reverse flow under 120□ for 2 hours and left to cool down to the room temperature. After filtering the mixture, the filtrate is dried by using a rotary evaporator and then removed impurities by dichloromethane. After filtering once more, the precipitate is collected and washed by ethanol, so as to obtain the ivory compound No. 12.

The compound No. 12 has the following characteristics: Mol. Wt.: 382.9262 ($C_{21}H_{15}ClOS_2$); $R_f$: 0.65 (ethyl acetate: n-hexane=1:6); Yield: 30%; Mp.: 215-216□ (ethanol); HRMS (EI) m/z: calcd, 382.0253 [M]$^+$; found, 382.0259; 1H-NMR (300 MHz, CDCl$_3$) δ(ppm): 2.42 (s, 6H, —CH$_3$), 6.48 (d, J=8.7 Hz, 1H, Ar—H), 7.28-7.37 (m, 3H, Ar—H), 7.47-7.53 (m, 1H, Ar—$H_6$), 7.65-7.66 (m, 2H, Ar—$H_{5,7}$), 8.28 (d, J=8.7 Hz, 1H, Ar—$H_1$), 8.54 (d, J=7.8 Hz, 1H, Ar—$H_8$); 13C-NMR (300 MHz, CDCl$_3$) δ (ppm): 21.46, 122.21, 126.57, 126.86, 127.66, 128.38, 128.61, 129.09, 129.81, 130.55, 132.55, 136.73, 137.61, 144.42, 179.50 (CO).

Embodiment 12 (4-Chloro-3-(3,4-dimethylphenylthio)-9H-thioxanthen-9-one, No. 13)

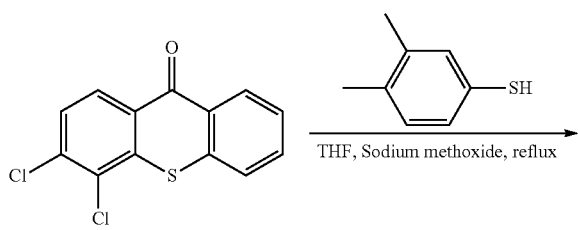

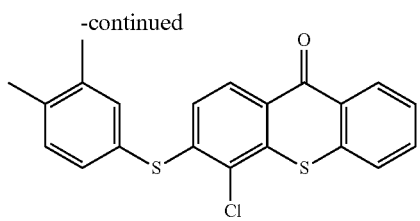

3,4-Dimethylbenzenethiol (2 mmol) with appropriate amount is slowly dropped into 10 mL of methanol contained sodium methoxide (0.108 g, 2 mmol). The abovementioned solution is stirred under room temperature, and 10 mL of tetrahydrofuran solution contained the compound No. 1 (0.28 g, 1 mmol) is slowly dropped thereinto. The mixture is then treated by a reverse flow under 120□ for 2 hours and left to cool down to the room temperature. After filtering the mixture, the filtrate is dried by using a rotary evaporator and then removed impurities by dichloromethane. After filtering once more, the precipitate is collected and washed by ethanol, so as to obtain the white compound No. 13.

The compound No. 13 has the following characteristics: Mol. Wt.: 382.9262 ($C_{21}H_{15}ClOS_2$); $R_f$: 0.57 (ethyl acetate:n-hexane=1:6); Yield: 42%; Mp.: 192-193□ (ethanol); HRMS (EI) m/z: calcd, 382.0253 $[M]^+$; found, 382.0259; 1H-NMR (300 MHz, $CDCl_3$) δ(ppm): 2.32 (d, J=10.8 Hz, 6H, —$CH_3$), 6.76 (d, J=8.7 Hz, 1H, Ar—$H_2$), 7.25-7.27 (m, 1H, Ar—H), 7.32-7.37 (m, 2H, Ar—H), 7.47-7.53 (m, 1H, Ar—$H_6$), 7.64-7.66 (m, 2H, Ar—$H_{5,7}$), 8.31 (d, J=9.0 Hz, 1H, Ar—$H_1$), 8.55 (dt, J=7.8 Hz, J=0.9 Hz, 1H, Ar—$H_8$); 13C-NMR (300 MHz, $CDCl_3$) (ppm): 19.48, 19.51, 123.83, 124.73, 126.12, 126.56, 126.84, 127.72, 128.12, 128.57, 129.78, 131.50, 132.52, 133.32, 136.80, 137.40, 138.91, 139.29, 146.20, 179.49 (CO).

Embodiment 13 (4-Chloro-3-(3,5-dimethylphenylthio)-9H-thioxanthen-9-one, No. 14)

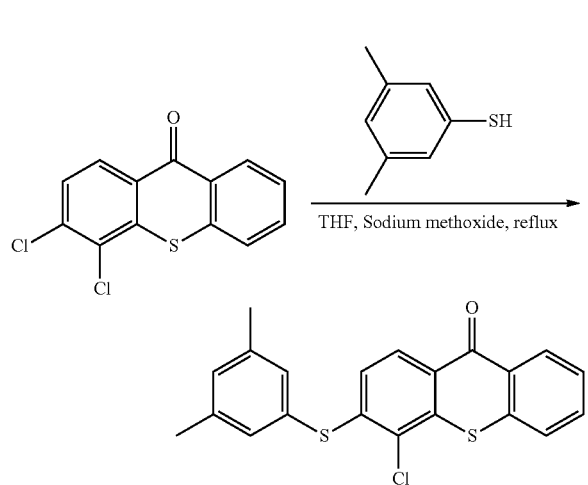

3,5-Dimethylbenzenethiol (2 mmol) with appropriate amount is slowly dropped into 10 mL of methanol contained sodium methoxide (0.108 g, 2 mmol). The abovementioned solution is stirred under room temperature, and 10 mL of tetrahydrofuran solution contained the compound No. 1 (0.28 g, 1 mmol) is slowly dropped thereinto. The mixture is then treated by a reverse flow under 120□ for 2 hours and left to cool down to the room temperature. After filtering the mixture, the filtrate is dried by using a rotary evaporator and then removed impurities by dichloromethane. After filtering once more, the precipitate is collected and washed by ethanol, so as to obtain the white compound No. 14.

The compound No. 14 has the following characteristics: Mol. Wt.: 382.9262 ($C_{21}H_{15}ClOS_2$); $R_f$: 0.61 (ethyl acetate:n-hexane=1:6); Yield: 46%; Mp.: 183-184□ (ethanol); HRMS (EI) m/z: calcd, 382.0253 $[M]^+$; found, 382.0249; 1H-NMR (300 MHz, $CDCl_3$) δ(ppm): 2.36 (d, J=0.6 Hz, 6H, —$CH_3$), 6.81 (d, J=8.4 Hz, 1H, Ar—$H_2$), 7.14-7.22 (m, 3H, Ar—H), 7.48-7.53 (m, 1H, Ar—$H_6$), 7.64-7.66 (m, 2H, Ar—$H_{5,7}$), 8.33 (d, J=9.0 Hz 1H, Ar—$H_1$), 8.55 (dt, J=8.1 Hz, J=0.9 Hz, 1H, Ar—$H_8$); 13C-NMR (300 MHz, $CDCl_3$) δ (ppm): 21.04, 124.20, 125.07, 126.59, 126.88, 127.88, 128.19, 128.62, 129.23, 129.83, 131.91, 132.56, 133.19, 136.81, 137.45, 140.07, 145.85, 179.53 (CO).

Embodiment 14 (4-Chloro-3-(2-methoxylphenylthio)-9H-thioxanthen-9-one, No. 15)

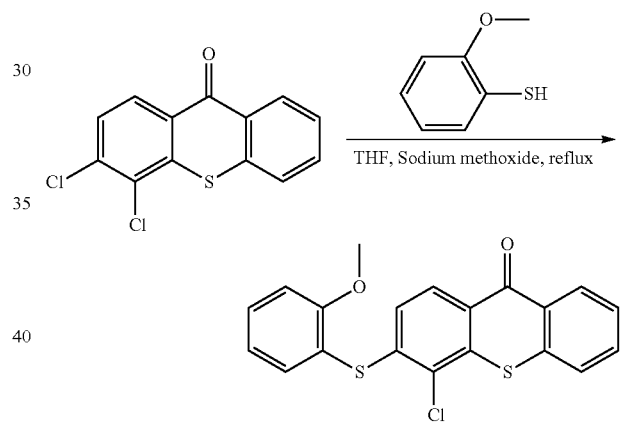

2-Methoxylbenzenethiol (2 mmol) with appropriate amount is slowly dropped into 10 mL of methanol contained sodium methoxide (0.108 g, 2 mmol). The abovementioned solution is stirred under room temperature, and 10 mL of tetrahydrofuran solution contained the compound No. 1 (0.28 g, 1 mmol) is slowly dropped thereinto. The mixture is then treated by a reverse flow under 120□ for 2 hours and left to cool down to the room temperature. After filtering the mixture, the filtrate is dried by using a rotary evaporator and then removed impurities by dichloromethane. After filtering once more, the precipitate is collected and washed by ethanol, so as to obtain the white compound No. 15.

The compound No. 15 has the following characteristics: Mol. Wt.: 384.8990 ($C_{20}H_{13}ClO_2S_2$); $R_f$: 0.39 (ethyl acetate:n-hexane=1:6); Yield: 58%; Mp.: 181-183□ (ethanol); HRMS (EI) m/z: calcd, 384.0045 $[M]^+$; found, 384.0038; 1H-NMR (300 MHz, $CDCl_3$) δ(ppm): 3.82 (s, 3H, —$OCH_3$), 6.71 (d, J=8.7 Hz, 1H, Ar—$H_2$), 7.05-7.10 (m, 2H, Ar—H), 7.47-7.60 (m, 3H, Ar—H), 7.62-7.66 (m, 2H, Ar—$H_{5,7}$), 8.31 (d, J=8.7 Hz, 1H, Ar—$H_1$), 8.55 (dt, J=8.1 Hz, J=0.9 Hz, 1H, Ar—$H_8$); 13C-NMR (300 MHz, $CDCl_3$) δ (ppm): 55.90, 55.95, 110.72, 111.99, 121.41, 121.85, 123.57, 126.54, 126.79, 127.87, 127.91, 128.01, 128.47, 129.72, 132.40, 132.51, 136.74, 137.57, 144.64, 160.36, 179.53 (CO).

Embodiment 15 (4-Chloro-3-(3-methoxyphenylthio)-9H-thioxanthen-9-one, No. 16)

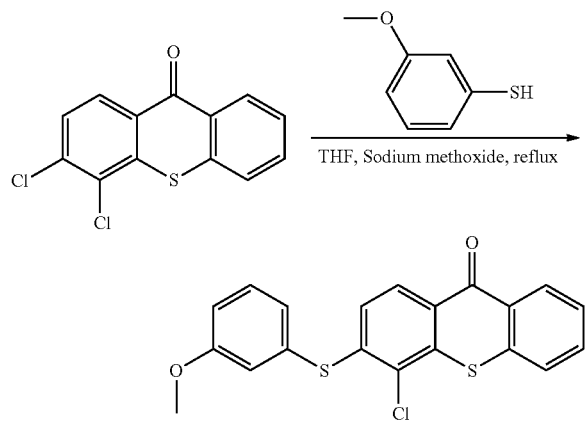

3-Methoxylbenzenethiol (2 mmol) with appropriate amount is slowly dropped into 10 mL of methanol contained sodium methoxide (0.108 g, 2 mmol). The abovementioned solution is stirred under room temperature, and 10 mL of tetrahydrofuran solution contained the compound No. 1 (0.28 g, 1 mmol) is slowly dropped thereinto. The mixture is then treated by a reverse flow under 120□ for 2 hours and left to cool down to the room temperature. After filtering the mixture, the filtrate is dried by using a rotary evaporator and then removed impurities by dichloromethane. After filtering once more, the precipitate is collected and washed by ethanol, so as to obtain the white compound No. 16.

The compound No. 16 has the following characteristics: Mol. Wt.: 384.8990 ($C_{20}H_{13}ClO_2S_2$); $R_f$: 0.49 (ethyl acetate: n-hexane=1:6); Yield: 44%; Mp.: 208-209□ (ethanol); HRMS (EI) m/z: calcd, 384.0045 [M]$^+$; found, 384.0045; 1H-NMR (300 MHz, CDCl$_3$) δ(ppm): 3.83 (s, 3H, —OCH$_3$), 6.84 (d, J=8.7 Hz, 1H, Ar—H$_2$), 7.03-7.07 (m, 1H, Ar—H), 7.12-7.14 (m, 1H, Ar—H), 7.17-7.20 (m, 1H, Ar—H), 7.38-7.44 (m, 1H, Ar—H), 7.48-7.53 (m, 1H, Ar—H$_6$), 7.63-7.66 (m, 2H, Ar—H$_{5,7}$), 8.33 (d, J=8.4 Hz, 1H, Ar—H$_1$), 8.55 (dt, J=8.1 Hz, J=0.9 Hz, 1H, Ar—H$_8$); 13C-NMR (300 MHz, CDCl$_3$) δ (ppm): 55.34, 55.45, 114.76, 115.55, 115.92, 119.74, 123.38, 126.58, 126.86, 127.64, 128.15, 128.55, 129.79, 132.56, 132.70, 136.73, 137.41, 137.75, 146.57, 161.58, 179.52 (CO).

Embodiment 16 (4-Chloro-3-(4-methoxyphenylthio)-9H-thioxanthen-9-one, No. 17)

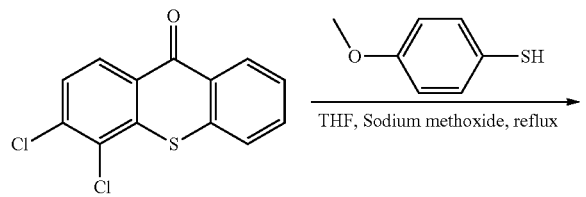

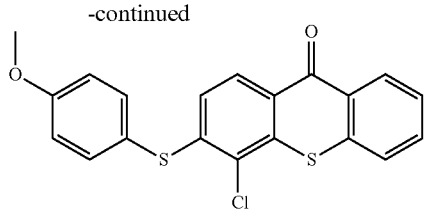

4-Methoxylbenzenethiol (2 mmol) with appropriate amount is slowly dropped into 10 mL of methanol contained sodium methoxide (0.108 g, 2 mmol). The abovementioned solution is stirred under room temperature, and 10 mL of tetrahydrofuran solution contained the compound No. 1 (0.28 g, 1 mmol) is slowly dropped thereinto. The mixture is then treated by a reverse flow under 120□ for 2 hours and left to cool down to the room temperature. After filtering the mixture, the filtrate is dried by using a rotary evaporator and then removed impurities by dichloromethane. After filtering once more, the precipitate is collected and washed by ethanol, so as to obtain the white compound No. 17.

The compound No. 17 has the following characteristics: Mol. Wt.: 384.8990 ($C_{20}H_{13}ClO_2S_2$); $R_f$: 0.67 (ethyl acetate: n-hexane=1:6); Yield: 65%; Mp.: 163-165□ (ethanol); HRMS (EI) m/z: calcd, 384.0045 [M]$^+$; found, 384.0046; 1H-NMR (300 MHz, CDCl$_3$) δ(ppm) 3.89 (s, 3H, —OCH$_3$), 6.72 (d, J=9.0 Hz, 1H, Ar—H$_2$), 7.00-7.05 (m, 2H, Ar—H), 7.47-7.55 (m, 3H, Ar—H), 7.64-7.66 (m, 2H, Ar—H$_{57}$), 8.31 (d, J=8.4 Hz, 1H, Ar—H$_1$), 8.55 (dt, J=8.1 Hz, J=0.9 Hz, 1H, Ar—H$_8$); 13C-NMR (300 MHz, CDCl$_3$) δ (ppm): 55.46, 116.21, 120.46, 124.21, 126.56, 126.89, 127.63, 128.00, 128.24, 128.50, 129.79, 129.94, 130.84, 130.96, 132.58, 136.71, 137.50, 145.14, 160.90, 179.45 (CO).

Embodiment 17 (4-Chloro-3-(2-ethylphenylthio)-9H-thioxanthen-9-one, No. 18)

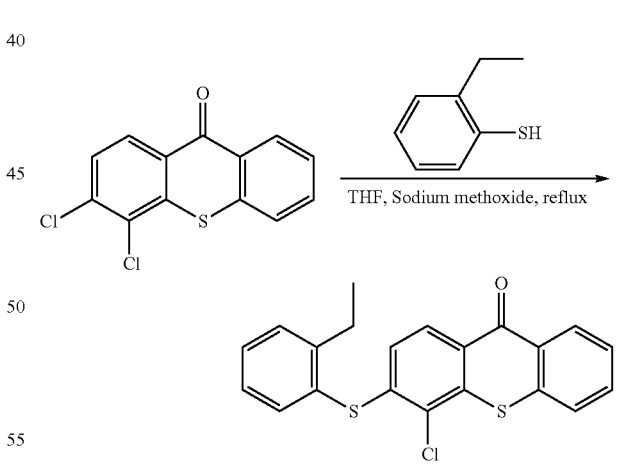

2-Ethylbenzenethiol (2 mmol) with appropriate amount is slowly dropped into 10 mL of methanol contained sodium methoxide (0.108 g, 2 mmol). The abovementioned solution is stirred under room temperature, and 10 mL of tetrahydrofuran solution contained the compound No. 1 (0.28 g, 1 mmol) is slowly dropped thereinto. The mixture is then treated by a reverse flow under 120□ for 2 hours and left to cool down to the room temperature. After filtering the mixture, the filtrate is dried by using a rotary evaporator and then removed impurities by dichloromethane. After filtering once more, the precipitate is collected and washed by ethanol, so as to obtain the white compound No. 18.

The compound No. 18 has the following characteristics: Mol. Wt.: 382.9262 ($C_{21}H_{15}ClOS_2$); $R_f$: 0.39 (ethyl acetate: n-hexane=1:6); Yield: 61%; Mp.: 165-166□ (ethanol); HRMS (EI) m/z: calcd, 382.0253 $[M]^+$; found, 382.0252; 1H-NMR (300 MHz, $CDCl_3$) δ(ppm): 1.19 (t, J=7.8 Hz, 3H, —$CH_3$), 2.78 (q, J=7.8 Hz, 2H, —$CH_2$—), 6.61 (d, J=8.7 Hz, 1H, Ar—$H_2$), 7.29-7.35 (m, 1H, Ar—H), 7.43-7.53 (m, 2H, Ar—H), 7.72 (dd, J=9.6 Hz, J=1.2 Hz, 1H, Ar—H), 7.65-7.66 (m, 2H, Ar—$H_{5,7}$), 8.30 (d, J=8.7 Hz, 1H, Ar—$H_1$), 8.55 (dt, J=8.1 Hz, J=0.9 Hz, 1H, Ar—$H_8$); 13C-NMR (300 MHz, $CDCl_3$) δ (ppm): 15.10, 27.25, 29.61, 123.44, 126.59, 126.89, 127.68, 128.23, 128.53, 129.81, 130.03, 131.06, 132.59, 136.73, 137.48, 145.58, 149.21, 179.53 (CO).

Embodiment 18 (4-Chloro-3-(3-ethoxylphenylthio)-9H-thioxanthen-9-one, No. 19)

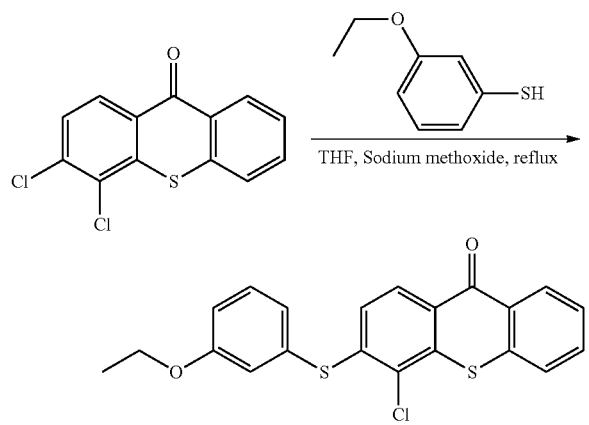

3-Ethoxylbenzenethiol (2 mmol) with appropriate amount is slowly dropped into 10 mL of methanol contained sodium methoxide (0.108 g, 2 mmol). The abovementioned solution is stirred under room temperature, and 10 mL of tetrahydrofuran solution contained the compound No. 1 (0.28 g, 1 mmol) is slowly dropped thereinto. The mixture is then treated by a reverse flow under 120□ for 2 hours and left to cool down to the room temperature. After filtering the mixture, the filtrate is dried by using a rotary evaporator and then removed impurities by dichloromethane. After filtering once more, the precipitate is collected and washed by ethanol, so as to obtain the white compound No. 19.

The compound No. 19 has the following characteristics: Mol. Wt.: 398.9256 ($C_{21}H_{15}ClO_2S_2$); $R_f$: 0.59 (ethyl acetate: n-hexane=1:6); Yield: 63%; Mp.: 149-150□ (ethanol); HRMS (EI) m/z: calcd, 398.0202 $[M]^+$; found, 398.0204; 1H-NMR (300 MHz, $CDCl_3$) δ(ppm): 1.43 (t, J=7.2 Hz, 3H, —$CH_3$), 4.05 (q, J=7.2 Hz, 2H, —$CH_2$—), 6.85 (d, J=8.7 Hz, 1H, Ar—$H_2$), 7.01-7.19 (m, 3H, Ar—H), 7.40 (t, J=8.1 Hz, 1H, Ar—H), 7.48-7.53 (m, 1H, Ar—$H_6$), 7.65-7.67 (m, 2H, Ar—$H_{5,7}$), 8.34 (d, J=8.7 Hz, 1H, Ar—$H_1$), 8.55 (dt, J=8.1 Hz, J=0.9 Hz, 1H, Ar—$H_8$); 13C-NMR (300 MHz, $CDCl_3$) δ (ppm): 14.57, 29.60, 63.82, 116.81, 121.03, 124.18, 126.59, 126.92, 127.53, 127.95, 128.25, 128.51, 129.81, 130.97, 132.61, 136.73, 137.49, 145.33, 160.25, 179.52 (CO).

Embodiment 19 (4-Chloro-3-(4-isopropylphenylthio)-9H-thioxanthen-9-one, No. 20)

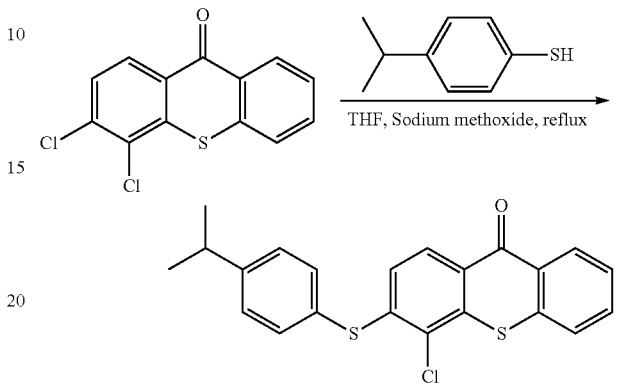

4-Isopropylbenzenethiol (2 mmol) with appropriate amount is slowly dropped into 10 mL of methanol contained sodium methoxide (0.108 g, 2 mmol). The abovementioned solution is stirred under room temperature, and 10 mL of tetrahydrofuran solution contained the compound No. 1 (0.28 g, 1 mmol) is slowly dropped thereinto. The mixture is then treated by a reverse flow under 120□ for 2 hours and left to cool down to the room temperature. After filtering the mixture, the filtrate is dried by using a rotary evaporator and then removed impurities by dichloromethane. After filtering once more, the precipitate is collected and washed by ethanol, so as to obtain the white compound No. 20.

The compound No. 20 has the following characteristics: Mol. Wt.: 396.9527 ($C_{22}H_{17}ClOS_2$); $R_f$: 0.58 (ethyl acetate: n-hexane=1:6); Yield: 71%; Mp.: 160-161□ (ethanol); HRMS (EI) m/z: calcd, 396.0409 $[M]^+$; found, 396.0409; 1H-NMR (300 MHz, $CDCl_3$) δ(ppm): 1.31 (d, J=6.9 Hz, 6H, —$CH_3$), 3.00 (q, J=6.9 Hz, 1H, —CH—), 6.78 (d, J=9.0 Hz, 1H, Ar—$H_2$), 7.36 (dd, J=6.0 Hz, J=1.5 Hz, 1H, Ar—H), 7.47-7.54 (m, 3H, Ar—H), 7.64-7.66 (m, 2H, Ar—$H_{5,7}$), 8.32 (d, J=8.7 Hz, 1H, Ar—$H_1$), 8.55 (dt, J=7.8 Hz, J=0.9 Hz, 1H, Ar—$H_8$); 13C-NMR (300 MHz, $CDCl_3$) δ (ppm): 23.69, 33.98, 123.88, 126.37, 126.59, 126.88, 127.84, 128.20, 128.44, 128.59, 129.82, 132.57, 135.86, 136.79, 137.47, 145.98, 151.52, 179.53 (CO).

Embodiment 20 (4-Chloro-3-(2-isopropylphenylthio)-9H-thioxanthen-9-one, No. 21)

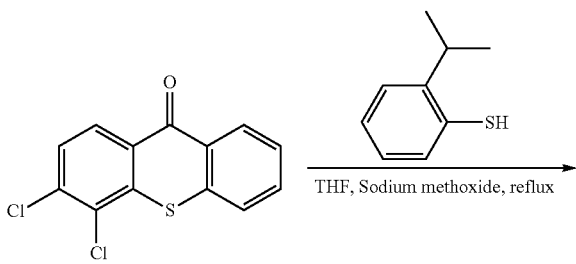

-continued

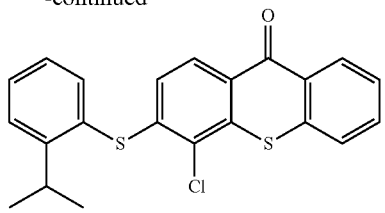

2-Isopropylbenzenethiol (2 mmol) with appropriate amount is slowly dropped into 10 mL of methanol contained sodium methoxide (0.108 g, 2 mmol). The abovementioned solution is stirred under room temperature, and 10 mL of tetrahydrofuran solution contained the compound No. 1 (0.28 g, 1 mmol) is slowly dropped thereinto. The mixture is then treated by a reverse flow under 120□ for 2 hours and left to cool down to the room temperature. After filtering the mixture, the filtrate is dried by using a rotary evaporator and then removed impurities by dichloromethane. After filtering once more, the precipitate is collected and washed by ethanol, so as to obtain the white compound No. 21.

The compound No. 21 has the following characteristics: Mol. Wt.: 396.9527 ($C_{22}H_{17}ClOS_2$); $R_f$: 0.63 (ethyl acetate:n-hexane=1:6); Yield: 59%; Mp.: 152-153□ (ethanol); HRMS (EI) m/z: calcd, 396.0409 [M]$^+$; found, 396.0404; 1H-NMR (300 MHz, CDCl$_3$) δ(ppm): 1.20 (d, J=6.9 Hz, 6H, —CH$_3$), 3.47 (q, J=6.9 Hz, 1H, —CH—), 6.60 (d, J=8.7 Hz, 1H, Ar—H$_2$), 7.27-7.33 (m, 1H, Ar—H), 7.47-7.59 (m, 4H, Ar—H), 7.63-7.65 (m, 2H, Ar—H$_{5,7}$), 8.30 (d, J=8.4 Hz, 1H, Ar—H$_1$), 8.54 (dt, J=8.1 Hz, J=0.9 Hz, 1H, Ar—H$_8$); 13C-NMR (300 MHz, CDCl$_3$) δ (ppm): 23.71, 29.62, 31.08, 123.60, 126.58, 126.88, 127.26, 127.50, 127.75, 128.20, 128.61, 129.83, 131.25, 132.56, 136.75, 137.48, 145.90, 153.73, 179.52 (CO).

Embodiment 21 (3-(4-Bromophenylthio)-4-chloro-9H-thioxanthen-9-one, No. 22)

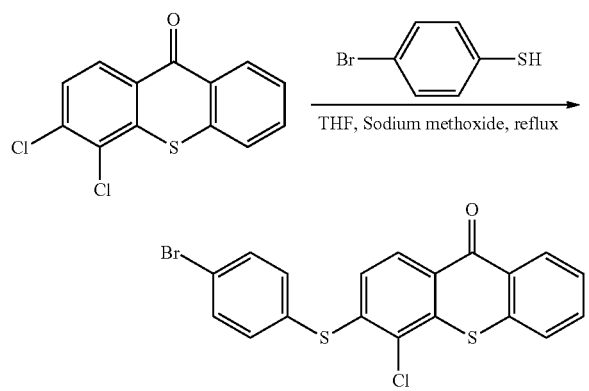

4-Bromobenzenethiol (2 mmol) with appropriate amount is slowly dropped into 10 mL of methanol contained sodium methoxide (0.108 g, 2 mmol). The abovementioned solution is stirred under room temperature, and 10 mL of tetrahydrofuran solution contained the compound No. 1 (0.28 g, 1 mmol) is slowly dropped thereinto. The mixture is then treated by a reverse flow under 120□ for 2 hours and left to cool down to the room temperature. After filtering the mixture, the filtrate is dried by using a rotary evaporator and then removed impurities by dichloromethane. After filtering once more, the precipitate is collected and washed by ethanol, so as to obtain the white compound No. 22.

The compound No. 22 has the following characteristics: Mol. Wt.: 433.7691 ($C_{19}H_{10}BrClOS_2$); $R_f$: 0.47 (ethyl acetate:n-hexane=1:6); Yield: 48%; Mp.: 222-223□ (ethanol); HRMS (EI) m/z: calcd, 431.9045 [M]$^+$; found, 433.9023; 1H-NMR (300 MHz, CDCl$_3$) δ(ppm): 6.82 (d, J=8.7 Hz, 1H, Ar—H$_2$), 7.43-7.54 (m, 3H, Ar—H), 7.61-7.67 (m, 4H, Ar—H), 8.35 (d, J=8.4 Hz, 1H, Ar—H$_1$), 8.567 (dt, J=8.1 Hz, J=0.9 Hz, 1H, Ar—H$_8$); 13C-NMR (300 MHz, CDCl$_3$) δ (ppm): 124.40, 126.62, 127.03, 128.46, 129.90, 132.72, 133.48, 136.74, 179.48 (CO).

Embodiment 22 (3-(Benzylthio)-4-chloro-9H-thioxanthen-9-one, No. 23)

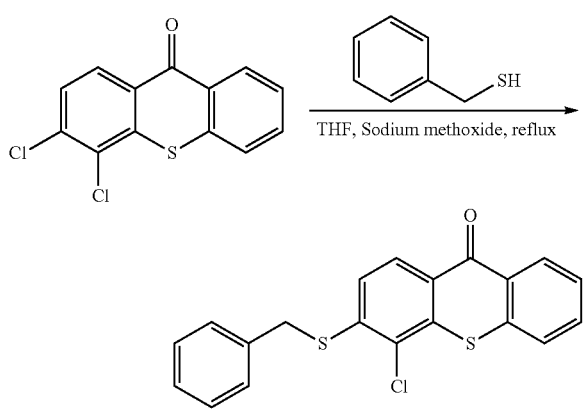

Phenylmethanethiol (2 mmol) with appropriate amount is slowly dropped into 10 mL of methanol contained sodium methoxide (0.108 g, 2 mmol). The abovementioned solution is stirred under room temperature, and 10 mL of tetrahydrofuran solution contained the compound No. 1 (0.28 g, 1 mmol) is slowly dropped thereinto. The mixture is then treated by a reverse flow under 120□ for 2 hours and left to cool down to the room temperature. After filtering the mixture, the filtrate is dried by using a rotary evaporator and then removed impurities by dichloromethane. After filtering once more, the precipitate is collected and washed by ethanol, so as to obtain the white compound No. 23.

The compound No. 23 has the following characteristics: Mol. Wt.: 368.8996 ($C_{20}H_{13}ClOS_2$); $R_f$: 0.36 (ethyl acetate:n-hexane=1:6); Yield: 41%; Mp.: 196-197□ (ethanol); HRMS (EI) m/z: calcd, 368.0096 [M]$^+$; found, 368.0097; 1H-NMR (300 MHz, CDCl$_3$) δ(ppm): 4.30 (s, 2H, —CH$_2$—), 7.27-7.38 (m, 4H, Ar—H), 7.43-7.46 (m, 2H, Ar—H), 7.47-7.53 (m, 1H, Ar—H$_6$), 7.61-7.66 (m, 2H, Ar—H$_{5,7}$), 8.47 (d, J=8.7 Hz, 1H, Ar—H$_1$), 8.56 (dt, J=8.1 Hz, J=0.9 Hz, 1H, Ar—H$_8$); 13C-NMR (300 MHz, CDCl$_3$) δ (ppm): 13.94, 22.58, 29.26, 29.61, 31.85, 36.78, 123.18, 126.58, 126.91, 127.97, 128.38, 128.46, 128.97, 128.99, 129.82, 132.65, 135.19, 136.79, 143.91, 179.59 (CO).

Embodiment 23 (4-Chloro-3-(4-fluorobenzylthio)-9H-thioxanthen-9-one, No. 24)

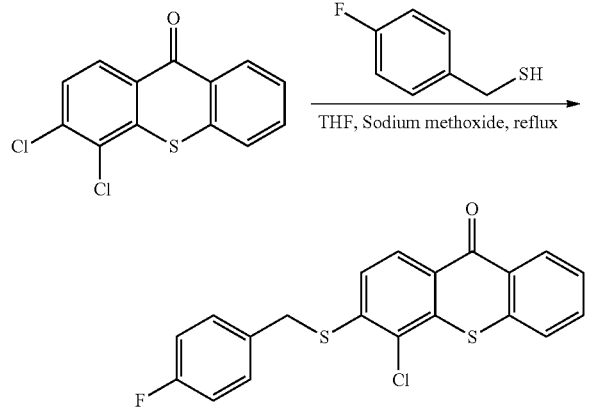

(4-Fluorophenyl)methanethiol (2 mmol) with appropriate amount is slowly dropped into 10 mL of methanol contained sodium methoxide (0.108 g, 2 mmol). The above-mentioned solution is stirred under room temperature, and 10 mL of tetrahydrofuran solution contained the compound No. 1 (0.28 g, 1 mmol) is slowly dropped thereinto. The mixture is then treated by a reverse flow under 120□ for 2 hours and left to cool down to the room temperature. After filtering the mixture, the filtrate is dried by using a rotary evaporator and then removed impurities by dichloromethane. After filtering once more, the precipitate is collected and washed by ethanol, so as to obtain the white compound No. 24.

The compound No. 24 has the following characteristics: Mol. Wt.: 386.8901 ($C_{20}H_{12}ClFOS_2$); $R_f$: 0.48 (ethyl acetate: n-hexane=1:6); Yield: 39%; Mp.: 230-231□ (ethanol); HRMS (EI) m/z: calcd, 386.0002 [M]$^+$; found, 386.0001; 1H-NMR (300 MHz, CDCl$_3$) δ(ppm): 4.28 (s, 2H, —CH$_2$—), 7.01-7.07 (m, 2H, Ar—H), 7.34 (d, J=8.7 Hz, 1H, Ar—H$_2$), 7.38-7.43 (m, 2H, Ar—H), 7.49-7.54 (m, 1H, Ar—H$_6$), 7.63-7.69 (m, 2H, Ar—H$_{5,7}$), 8.49 (d, J=8.7 Hz, 1H, Ar—H$_1$), 8.57 (dt, J=7.8 Hz, J=0.9 Hz, 1H, Ar—H$_8$); 13C-NMR (300 MHz, CDCl$_3$) δ (ppm): 29.15, 36.19, 115.57, 115.75, 116.04, 123.47, 126.59, 126.96, 128.08, 128.43, 128.53, 129.87, 130.59, 130.69, 131.07, 132.69, 136.80, 143.40, 179.56 (CO).

Embodiment 24 (3-(4-Bromobenzylthio)-4-chloro-9H-thioxanthen-9-one, No. 25)

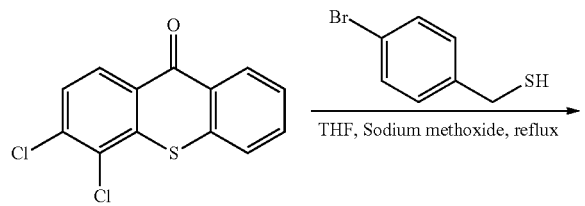

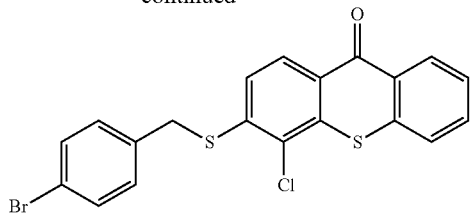

(4-Bromophenyl)methanethiol (2 mmol) with appropriate amount is slowly dropped into 10 mL of methanol contained sodium methoxide (0.108 g, 2 mmol). The above-mentioned solution is stirred under room temperature, and 10 mL of tetrahydrofuran solution contained the compound No. 1 (0.28 g, 1 mmol) is slowly dropped thereinto. The mixture is then treated by a reverse flow under 120□ for 2 hours and left to cool down to the room temperature. After filtering the mixture, the filtrate is dried by using a rotary evaporator and then removed impurities by dichloromethane. After filtering once more, the precipitate is collected and washed by ethanol, so as to obtain the white compound No. 25.

The compound No. 25 has the following characteristics: Mol. Wt.: 447.7956 ($C_{20}H_{12}ClBrOS_2$); $R_f$: 0.52 (ethyl acetate:n-hexane=1:6); Yield: 49%; Mp.: 248-249□ (ethanol); HRMS (EI) m/z: calcd, 445.9201 [M]$^+$; found, 445.9203; 1H-NMR (300 MHz, CDCl$_3$) δ(ppm): 4.25 (s, 2H, —CH$_2$—), 7.31 (d, J=8.7 Hz, 3H, Ar—H), 7.46-7.54 (m, 3H, Ar—H), 7.64-7.67 (m, 2H, Ar—H$_{5,7}$), 8.48 (d, J=8.4 Hz, 1H, Ar—H$_1$), 8.57 (d, J=7.8 Hz, 1H, Ar—H$_8$); 13C-NMR (300 MHz, CDCl$_3$) δ (ppm): 28.60, 42.28, 121.62, 122.98, 126.01, 126.43, 127.63, 127.97, 128.27, 129.30, 130.43, 131.23, 132.13, 134.25, 135.99, 136.88, 141.82, 178.94 (CO).

Embodiment 25 (4-Chloro-3-(4-chlorobenzylthio)-9H-thioxanthen-9-one, No. 26)

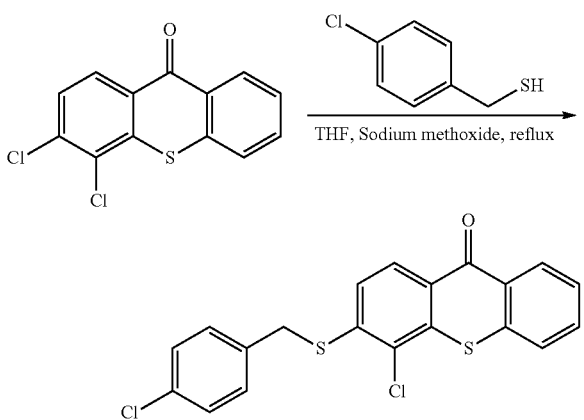

(4-Chlorophenyl)methanethiol (2 mmol) with appropriate amount is slowly dropped into 10 mL of methanol contained sodium methoxide (0.108 g, 2 mmol). The above-mentioned solution is stirred under room temperature, and 10 mL of tetrahydrofuran solution contained the compound No. 1 (0.28 g, 1 mmol) is slowly dropped thereinto. The mixture is then treated by a reverse flow under 120□ for 2 hours and left to cool down to the room temperature. After filtering the mixture, the filtrate is dried by using a rotary evaporator and then removed impurities by dichloromethane. After filtering once more, the precipitate is collected and washed by ethanol, so as to obtain the white compound No. 26.

The compound No. 26 has the following characteristics: Mol. Wt.: 403.3446 ($C_{20}H_{12}Cl_2OS_2$); $R_f$: 0.66 (ethyl acetate: n-hexane=1:6); Yield: 65%; Mp.: 240-241□ (ethanol); HRMS (EI) m/z: calcd, 401.9707 $[M]^+$; found, 401.9705; 1H-NMR (300 MHz, $CDCl_3$) δ(ppm): 4.27 (s, 2H, —$CH_2$—), 7.31-7.39 (m, 5H, Ar—H), 7.49-7.54 (m, 1H, Ar—$H_6$), 7.64-7.67 (m, 2H, Ar—$H_{5,7}$), 8.48 (d, J=8.7 Hz, 1H, Ar—$H_1$), 8.57 (d, J=7.5 Hz, 1H, Ar—$H_8$); 13C-NMR (300 MHz, $CDCl_3$) δ (ppm): 29.17, 29.62, 36.26, 123.54, 126.61, 126.98, 128.47, 128.92, 129.20, 129.89, 130.30, 130.75, 132.72, 158.05, 179.57 (CO).

Embodiment 26 (4-Chloro-3-(4-methoxybenzylthio)-9H-thioxanthen-9-one, No. 27)

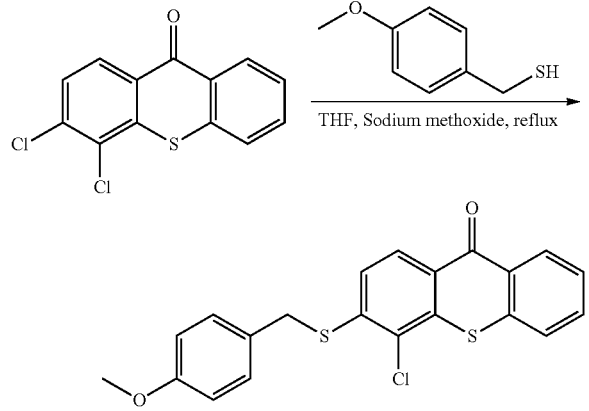

(4-Methoxyphenyl)methanethiol (2 mmol) with appropriate amount is slowly dropped into 10 mL of methanol contained sodium methoxide (0.108 g, 2 mmol). The above-mentioned solution is stirred under room temperature, and 10 mL of tetrahydrofuran solution contained the compound No. 1 (0.28 g, 1 mmol) is slowly dropped thereinto. The mixture is then treated by a reverse flow under 120□ for 2 hours and left to cool down to the room temperature. After filtering the mixture, the filtrate is dried by using a rotary evaporator and then removed impurities by dichloromethane. After filtering once more, the precipitate is collected and washed by ethanol, so as to obtain the white compound No. 27.

The compound No. 27 has the following characteristics: Mol. Wt.: 398.9256 ($C_{21}H_5ClO_2S_2$); $R_f$: 0.38 (ethyl acetate: n-hexane=1:6); Yield: 28%; Mp.: 202-203□ (ethanol); HRMS (EI) m/z: calcd, 398.0202 $[M]^+$; found, 398.0200; 1H-NMR (300 MHz, $CDCl_3$) δ(ppm): 3.80 (s, 3H, —$OCH_3$), 4.26 (s, 2H, —$CH_2$—), 6.83-6.91 (m, 2H, Ar—H), 7.34-7.38 (m, 3H, Ar—H), 7.48-7.53 (m, 1H, Ar—$H_6$), 7.62-7.65 (m, 2H, Ar—$H_{5,7}$), 8.48 (d, J=8.7 Hz, 1H, Ar—$H_1$), 8.56 (dt, J=8.1 Hz, J=0.9 Hz, 1H, Ar—$H_8$); 13C-NMR (300 MHz, $CDCl_3$) δ (ppm): 36.40, 55.31, 114.51, 123.37, 126.59, 126.90, 127.06, 127.85, 128.37, 128.57, 129.85, 130.19, 132.62, 136.85, 137.49, 144.11, 159.62, 179.59 (CO).

Embodiment 27 (4-Chloro-3-(2,4,6-trimethylbenzylthio)-9H-thioxanthen-9-one, No. 28)

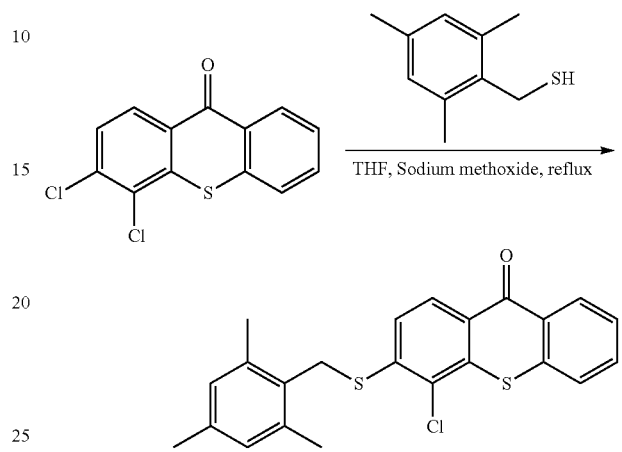

2,4,6-Trimethylbenzylmercaptan (2 mmol) with appropriate amount is slowly dropped into 10 mL of methanol contained sodium methoxide (0.108 g, 2 mmol). The above-mentioned solution is stirred under room temperature, and 10 mL of tetrahydrofuran solution contained the compound No. 1 (0.28 g, 1 mmol) is slowly dropped thereinto. The mixture is then treated by a reverse flow under 120□ for 2 hours and left to cool down to the room temperature. After filtering the mixture, the filtrate is dried by using a rotary evaporator and then removed impurities by dichloromethane. After filtering once more, the precipitate is collected and washed by ethanol, so as to obtain the white compound No. 28.

The compound No. 28 has the following characteristics: Mol. Wt.: 410.9793 ($C_{23}H_{19}ClOS_2$); $R_f$: 0.42 (ethyl acetate: n-hexane=1:6); Yield: 34%; Mp.: 214-215□ (ethanol); HRMS (EI) m/z: calcd, 410.0566 $[M]^+$; found, 410.0569; 1H-NMR (300 MHz, $CDCl_3$) δ(ppm): 2.29 (s, 3H, —$CH_3$), 2.42 (s, 6H, —$CH_3$), 4.28 (s, 2H, —$CH_2$—), 6.91 (s, 2H, Ar—H), 7.48 (d, J=8.7 Hz, 1H, Ar—$H_2$), 7.50-7.55 (m, 1H, Ar—$H_6$), 7.63-7.67 (m, 1H, Ar—$H_{5,7}$), 8.57-8.61 (m, 2H, Ar—$H_{18}$); 13C-NMR (300 MHz, $CDCl_3$) δ (ppm): 19.39, 20.84, 31.86, 123.17, 126.62, 126.92, 127.59, 128.52, 129.46, 129.88, 132.65, 136.88, 137.74, 137.88, 145.22, 179.65 (CO).

Embodiment 28 (4-Chloro-3-(4-chlorophenylthio)-9H-thioxanthen-9-one, No. 29)

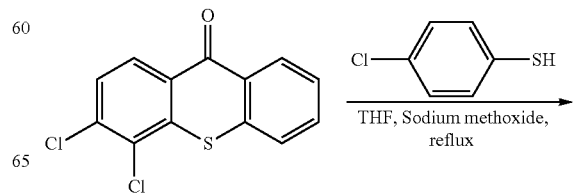

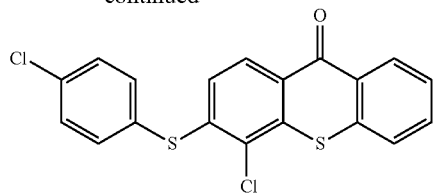

4-Chlorobenzenethiol (2 mmol) with appropriate amount is slowly dropped into 10 mL of methanol contained sodium methoxide (0.108 g, 2 mmol). The abovementioned solution is stirred under room temperature, and 10 mL of tetrahydrofuran solution contained the compound No. 1 (0.28 g, 1 mmol) is slowly dropped thereinto. The mixture is then treated by a reverse flow under 120□ for 2 hours and left to cool down to the room temperature. After filtering the mixture, the filtrate is dried by using a rotary evaporator and then removed impurities by dichloromethane. After filtering once more, the precipitate is collected and washed by ethanol, so as to obtain the white compound No. 29.

The compound No. 29 has the following characteristics: Mol. Wt.: 389.3181 ($C_{19}H_{10}Cl_2OS_2$); $R_f$: 0.64 (ethyl acetate: n-hexane=1:6); Yield: 47%; Mp.: 223-224□ (ethanol); HRMS (EI) m/z: calcd, 387.9550 [M]$^+$; found, 387.9551; 1H-NMR (300 MHz, CDCl$_3$) δ(ppm): 6.80 (d, J=8.7 Hz, 1H, Ar—H$_2$), 7.46-7.55 (m, 5H, Ar—H), 7.65-7.67 (m, 2H, Ar—H$_{5,7}$), 8.35 (d, J=9.0 Hz, 1H, Ar—H$_1$), 8.55 (dt, J=7.8 Hz, J=0.9 Hz, 1H, Ar—H$_8$); 13C-NMR (300 MHz, CDCl$_3$) δ (ppm): 124.21, 126.62, 127.02, 128.32, 128.43, 128.53, 128.62, 129.88, 130.52, 132.71, 136.65, 137.76, 144.38, 179.49 (CO).

Embodiment 29 (4-Chloro-3-(3-chlorophenylthio)-9H-thioxanthen-9-one, No. 30)

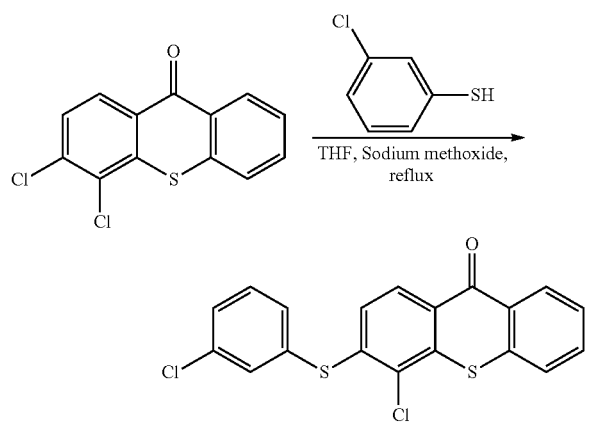

3-Chlorobenzenethiol (2 mmol) with appropriate amount is slowly dropped into 10 mL of methanol contained sodium methoxide (0.108 g, 2 mmol). The abovementioned solution is stirred under room temperature, and 10 mL of tetrahydrofuran solution contained the compound No. 1 (0.28 g, 1 mmol) is slowly dropped thereinto. The mixture is then treated by a reverse flow under 120□ for 2 hours and left to cool down to the room temperature. After filtering the mixture, the filtrate is dried by using a rotary evaporator and then removed impurities by dichloromethane. After filtering once more, the precipitate is collected and washed by ethanol, so as to obtain the white compound No. 30.

The compound No. 30 has the following characteristics: Mol. Wt.: 389.3181 ($C_{19}H_{10}Cl_2OS_2$); $R_f$: 0.53 (ethyl acetate: n-hexane=1:6); Yield: 55%; Mp.: 181-182□ (ethanol); HRMS (EI) m/z: calcd, 387.9550 [M]$^+$; found, 387.9551; 1H-NMR (300 MHz, CDCl$_3$) δ(ppm): 6.86 (d, J=8.7 Hz, 1H, Ar—H$_2$), 7.42-7.54 (m, 4H, Ar—H), 7.58-7.59 (m, 1H, Ar—H), 7.64-7.67 (m, 2H, Ar—H$_{57}$), 8.37 (d, J=8.7 Hz, 1H, Ar—H$_1$), 8.56 (dt, J=7.8 Hz, J=0.9 Hz, 1H, Ar—H$_8$); 13C-NMR (300 MHz, CDCl$_3$) δ (ppm): 124.63, 126.62, 127.04, 128.48, 129.87, 130.16, 131.15, 132.22, 132.74, 133.16, 134.76, 135.84, 136.69, 137.77, 143.79, 179.49 (CO).

Figure 3:
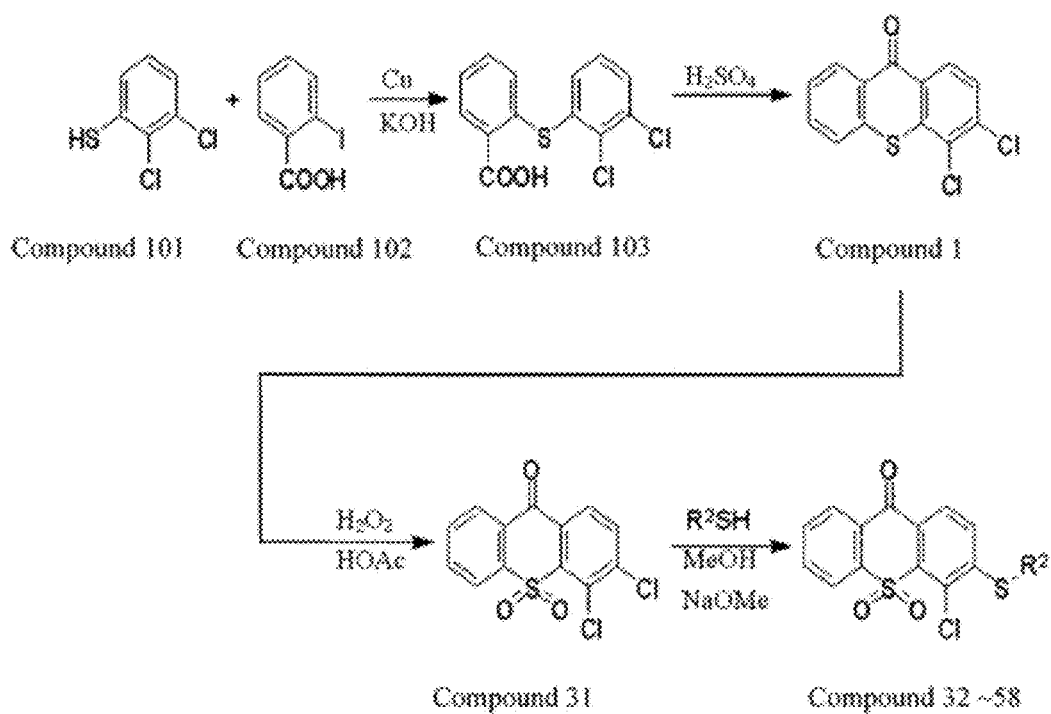
FIG. 3 is flow chart for manufacturing the compound No. 31~58.

FIG. 3 is a flow chart for manufacturing compounds No. 31-58. It clearly points out that the compound No. 31 can be obtained by oxidizing the compound No. 101. On the other words, the compound No. 31 can be a reactant for manufacturing a plurality of the thioxanthone ring system derivatives. The method for manufacturing the compound 31 comprises steps as follows: Compound No. 101 (3,4-dichloro-9H-thioxanthen-9-one) is dissolved in 20 mL of glacial acetate acid, and then 10 mL of hydrogen peroxide is added thereinto. After 2 hours of reacting by a reverse flow, the mixture is then transferred into 200 mL of ice water. After filtering, the compound No. 31 (3,4-dichloro-9H-thioxanthen-9-one 10,10-dioxide) is obtained. That is, $R^1$ presented in the formula I can be S (the compound No. 1) or $SO_2$ (the compound No. 31).

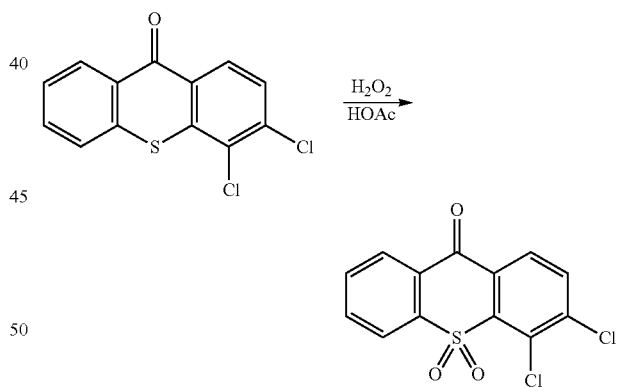

The compound No. 31 has the following characteristics: Mol. Wt.: 311.9415 ($C_{13}H_6Cl_2O_3S$); Melting Point (° C.): 234; HRMS (EI): 311.9415; 1H-NMR (300 MHz, CDCl$_3$), δ(ppm): 7.82 (td, J=7.5 Hz, 1.2 Hz, 1H), 7.87 (d, J=8.7 Hz, 1H), 7.95 (td, J=7.5 Hz, 1.2 Hz, 1H), 8.10 (d, J=8.1 Hz, 0.9 Hz, 1H), 8.32 (d, J=7.8 Hz, 1H), 8.36 (dd, J=8.1 Hz, 1.2 Hz, 1H); 13C-NMR (75 MHz, CDCl$_3$) δ(ppm).

According to the abovementioned compound No. 31, the method for manufacturing a plurality of the thioxanthone ring system derivatives by using the compound No. 31 as the reactant in the beginning and the analytic results about them will be disclosed with a series embodiments as follows.

Embodiment 30 (4-Chloro-3-(benzenethio)-9H-thioxanthen-9-one 10,10-dioxide, No. 32)

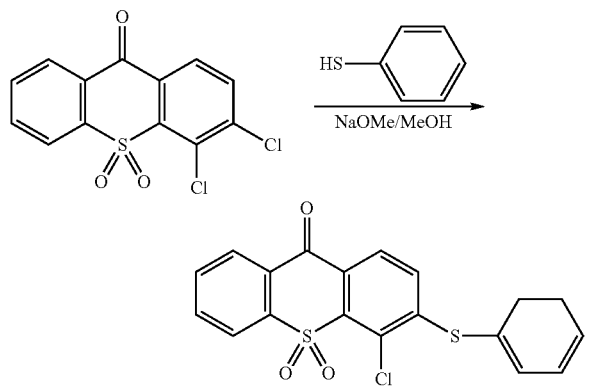

Benzenethiol (1 mmol) with appropriate amount is slowly dropped into 10 mL of methanol contained sodium methoxide (0.054 g, 1 mmol). The abovementioned solution is stirred under room temperature, and 20 mL of tetrahydrofuran solution contained the compound No. 31 (0.1 g, 0.35 mmol) is dropped thereinto. The mixture is then treated by a reverse flow for 2 hours. After drying the mixture, the precipitate is collected and washed by cold alcohol, so as to obtain the compound No. 32.

The compound No. 31 has the following characteristics: Mol. Wt.: 385.9838 ($C_{19}H_{11}ClO_3S_2$); Melting Point (° C.): 241.4 HRMS (EI): m/z: calcd: 385.9838, found: 385.9837; 1H-NMR (300 MHz, $CDCl_3$), δ(ppm): 6.94 (d, J=8.7 Hz, 1H), 7.50-7.62 (m, 5H), 7.78 (td, J=8.1 Hz, 1.2 Hz, 1H), 7.92 (td, J=7.5 Hz, 1.2 Hz, 1H), 8.08 (d, J=8.7 Hz, 1H), 8.18 (dd, J=7.8 Hz, 0.9 Hz, 1H), 8.32 (dd, J=7.8 Hz, 0.9 Hz, 1H); 13C-NMR (75 MHz, $CDCl_3$), δ(ppm): 123.85, 126.52, 127.83, 128.24, 128.63, 128.81, 129.01, 129.17, 130.62, 130.75, 133.12, 135.21, 136.06, 138.31, 142.56, 151.45, 176.81.

Embodiment 31 (4-Chloro-3-(4-chlorobenzenethio)-9H-thioxanthen-9-one 10,10-dioxide, No. 33)

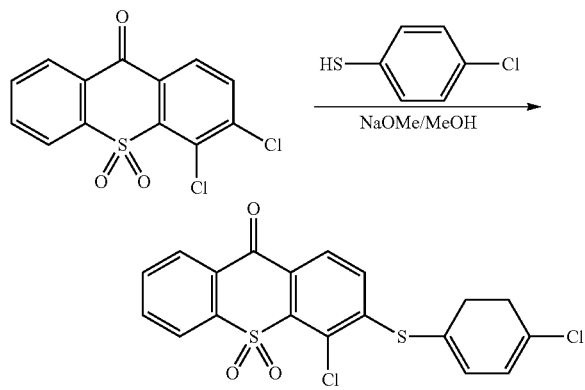

4-Chlorobenzenethiol (1 mmol) with appropriate amount is slowly dropped into 10 mL of methanol contained sodium methoxide (0.054 g, 1 mmol). The abovementioned solution is stirred under room temperature, and 20 mL of tetrahydrofuran solution contained the compound No. 31 (0.1 g, 0.35 mmol) is dropped thereinto. The mixture is then treated by a reverse flow for 2 hours. After drying the mixture, the precipitate is collected and washed by cold alcohol, so as to obtain the compound No. 33.

The compound No. 33 has the following characteristics: Mol. Wt.: 419.9448 ($C_{19}H_{10}Cl_2O_3S_2$); Melting Point (° C.): 250.0; HRMS (EI): 1H-NMR (300 MHz, $CDCl_3$), δ(ppm): 6.94 (d, J=8.7 Hz, 1H), 7.52-7.54 (m, 4H), 7.78 (td, J=8.1 Hz, 1.2 Hz, 1H), 7.92 (td, J=7.5 Hz, 1.2 Hz, 1H), 8.08 (d, J=8.7 Hz, 1H), 8.18 (dd, J=7.8 Hz, 0.9 Hz, 1H), 8.32 (dd, J=7.8 Hz, 0.9 Hz, 1H); 13C-NMR (75 MHz, $CDCl_3$), δ(ppm): 124.02, 126.95, 127.51, 128.11, 128.72, 128.83, 129.14, 129.35, 129.56, 131.07, 133.32, 135.41, 137.22, 137.36, 137.61, 138.65, 142.71, 150.71, 176.92.

Embodiment 32 (4-Chloro-3-(4-methylbenzenethio) 9H-thioxanthen-9-one 10,10-dioxide, No. 34)

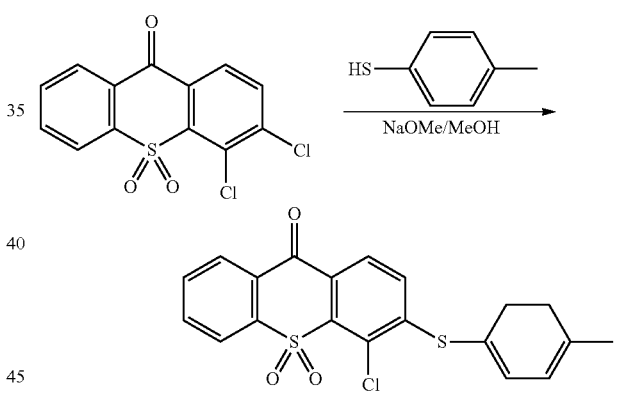

4-methylbenzenethiol (1 mmol) with appropriate amount is slowly dropped into 10 mL of methanol contained sodium methoxide (0.054 g, 1 mmol). The abovementioned solution is stirred under room temperature, and 20 mL of tetrahydrofuran solution contained the compound No. 31 (0.1 g, 0.35 mmol) is dropped thereinto. The mixture is then treated by a reverse flow for 2 hours. After drying the mixture, the precipitate is collected and washed by cold alcohol, so as to obtain the compound No. 34.

The compound No. 34 has the following characteristics: Mol. Wt.: 399.9995 ($C_{20}H_{13}ClO_3S_2$); Melting Point (° C.): 246.1; HRMS (EI): 1H-NMR (300 MHz, $CDCl_3$), δ(ppm): 6.93 (d, J=9 Hz, 1H), 7.34 (d, J=7.8 Hz, 2H), 7.47 (d, J=7.8 Hz, 2H), 7.78 (td, J=7.8 Hz, 1.2 Hz, 1H), 7.91 (td, J=7.8 Hz, 1.2 Hz, 1H), 8.07 (d, J=8.7 Hz, 1H), 8.18 (dd, J=8.1 Hz, 1.2 Hz, 1H), 8.32 (dd, J=8.1 Hz, 1.2 Hz, 1H); 13C-NMR (75 MHz, $CDCl_3$), δ(ppm): 21.46, 123.99, 125.22, 126.47, 127.92, 128.25, 128.76, 129.18, 131.58, 133.25, 135.33, 136.20, 138.40, 141.50, 142.74, 152.16, 177.00.

Embodiment 33 (3-(3-chlorophenylthio)-4-chloro-9H-thioxanthen-9-one 10,10-dioxide, No. 35)

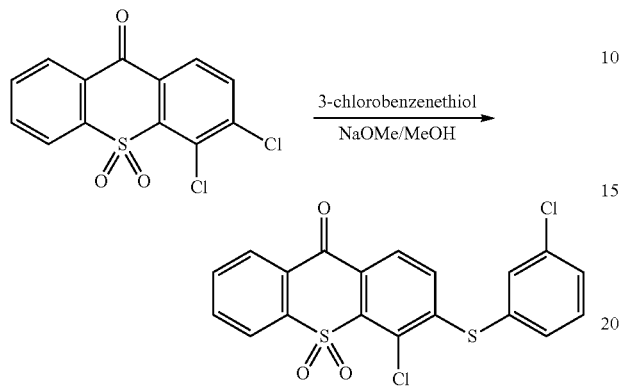

3-Chlorobenzenethiol (1 mmol) with appropriate amount is slowly dropped into 10 mL of methanol contained sodium methoxide (0.054 g, 1 mmol). The abovementioned solution is stirred under room temperature, and 20 mL of tetrahydrofuran solution contained the compound No. 31 (0.1 g, 0.35 mmol) is dropped thereinto. The mixture is then treated by a reverse flow for 2 hours. After drying the mixture, the precipitate is collected and washed by cold alcohol, so as to obtain the compound No. 35.

The compound No. 35 has the following characteristics: Mol. Wt.: 419.9448 ($C_{19}H_{10}Cl_2O_3S_2$); Melting Point (° C.): 262.7; HRMS (EI): 1H-NMR (300 MHz, CDCl$_3$), δ(ppm): 7.00 (d, J=8.7 Hz, 1H), 7.47-7.61 (m, 4H), 7.79 (td, J=7.8 Hz, 1.2 Hz, 1H), 7.92 (td, J=7.8 Hz, 1.2 Hz, 1H), 8.13 (d, J=8.7 Hz, 1H), 8.19 (dd, J=8.1 Hz, 0.9 Hz, 1H), 8.33 (dd, J=8.1 Hz, 1.2 Hz, 1H); 13C-NMR (75 MHz, CDCl$_3$), δ(ppm): 124.03, 128.18, 128.85, 129.15, 129.66, 131.10, 131.71, 133.32, 134.01, 135.43, 135.63, 136.40, 176.91.

Embodiment 34 (4-Chloro-3-(2-aminobenzenethio) 9H-thioxanthen-9-one 10,10-dioxide, No. 36)

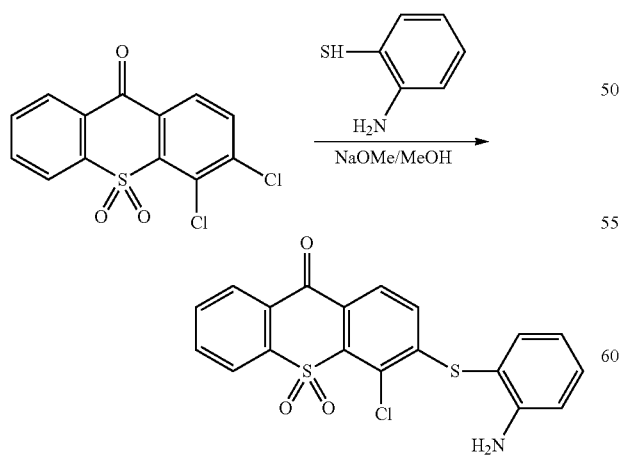

2-aminobenzenethiol (1 mmol) with appropriate amount is slowly dropped into 10 mL of methanol contained sodium methoxide (0.054 g, 1 mmol). The abovementioned solution is stirred under room temperature, and 20 mL of tetrahydrofuran solution contained the compound No. 31 (0.1 g, 0.35 mmol) is dropped thereinto. The mixture is then treated by a reverse flow for 2 hours. After drying the mixture, the precipitate is collected and washed by cold alcohol, so as to obtain the compound No. 36.

The compound No. 36 has the following characteristics: Mol. Wt.: 400.9947; Melting Point (° C.): 281.5.

Embodiment 35 (4-Chloro-3-((4-tert-butylphenyl)methanethio)-9H-thioxanthen-9-one10, 10-dioxide, No. 37)

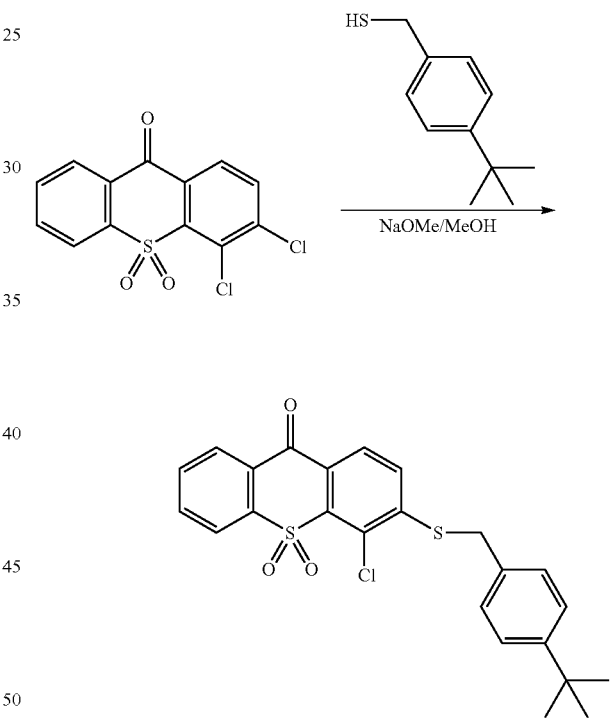

(4-tert-butylphenyl)methanethiol (1 mmol) with appropriate amount is slowly dropped into 10 mL of methanol contained sodium methoxide (0.054 g, 1 mmol). The abovementioned solution is stirred under room temperature, and 20 mL of tetrahydrofuran solution contained the compound No. 31 (0.1 g, 0.35 mmol) is dropped thereinto. The mixture is then treated by a reverse flow for 2 hours. After drying the mixture, the precipitate is collected and washed by cold alcohol, so as to obtain the compound No. 37.

The compound No. 37 has the following characteristics: Mol. Wt.: 456.0621; Melting Point (° C.): 284; 13C-NMR (75 MHz, CDCl₃), δ(ppm): 7.

Embodiment 36 (4-Chloro-3-(2-ethylbenzenethio) 9H-thioxanthen-9-one 10,10-dioxide, No. 38)

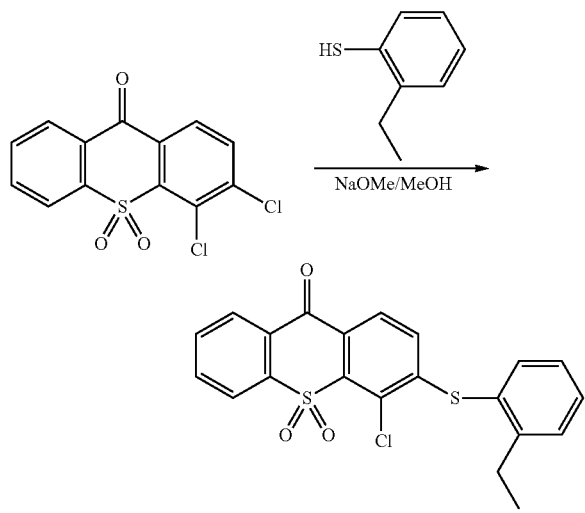

2-ethylbenzenethiol (1 mmol) with appropriate amount is slowly dropped into 10 mL of methanol contained sodium methoxide (0.054 g, 1 mmol). The abovementioned solution is stirred under room temperature, and 20 mL of tetrahydrofuran solution contained the compound No. 31 (0.1 g, 0.35 mmol) is dropped thereinto. The mixture is then treated by a reverse flow for 2 hours. After drying the mixture, the precipitate is collected and washed by cold alcohol, so as to obtain the compound No. 38.

The compound No. 38 has the following characteristics: Mol. Wt.: 414.0151; Melting Point (° C.): 215.5.

Embodiment 37 (4-Chloro-3-(2,4-dimethylbenzenethio) 9H-thioxanthen-9-one 10,10-dioxide, No. 39)

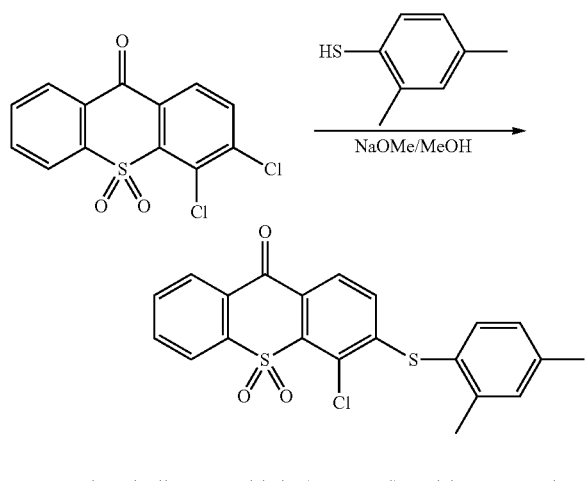

2,4-Dimethylbenzenethiol (1 mmol) with appropriate amount is slowly dropped into 10 mL of methanol contained sodium methoxide (0.054 g, 1 mmol). The abovementioned solution is stirred under room temperature, and 20 mL of tetrahydrofuran solution contained the compound No. 31 (0.1 g, 0.35 mmol) is dropped thereinto. The mixture is then treated by a reverse flow for 2 hours. After drying the mixture, the precipitate is collected and washed by cold alcohol, so as to obtain the compound No. 39.

The compound No. 39 has the following characteristics: Mol. Wt.: 414.0151; Melting Point (° C.): 235.6.

Embodiment 38 (4-Chloro-3-(2-methylbenzenethio)-9H-thioxanthen-9-one 10,10-dioxide, No. 40)

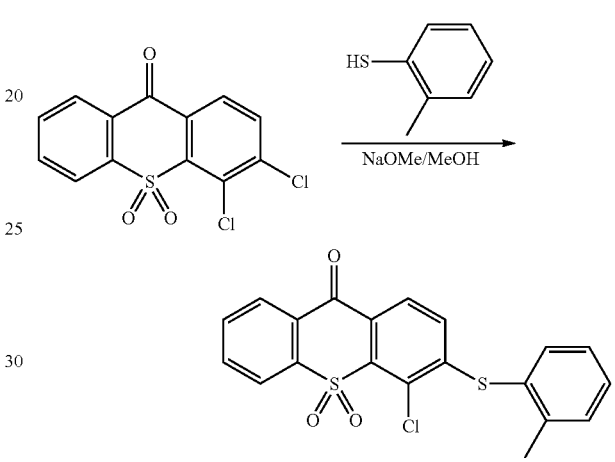

2-Methylbenzenethiol (1 mmol) with appropriate amount is slowly dropped into 10 mL of methanol contained sodium methoxide (0.054 g, 1 mmol). The abovementioned solution is stirred under room temperature, and 20 mL of tetrahydrofuran solution contained the compound No. 31 (0.1 g, 0.35 mmol) is dropped thereinto. The mixture is then treated by a reverse flow for 2 hours. After drying the mixture, the precipitate is collected and washed by cold alcohol, so as to obtain the compound No. 40.

The compound No. 40 has the following characteristics: Mol. Wt.: 399.9995; Melting Point (° C.): 255.6.

Embodiment 39 (4-Chloro-3-(2,6-dimethylbenzenethio)9H-thioxanthen-9-one 10,10-dioxide, No. 41)

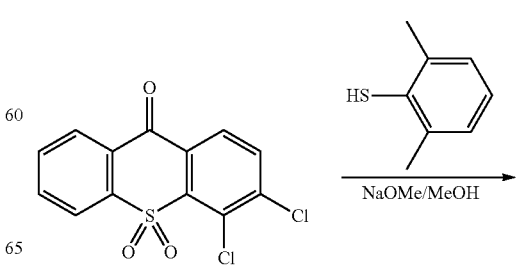

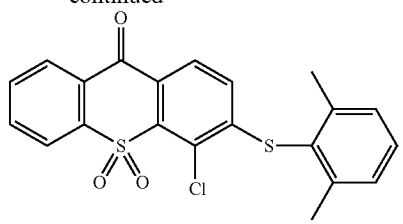

2,6-dimethylbenzenethiol (1 mmol) with appropriate amount is slowly dropped into 10 mL of methanol contained sodium methoxide (0.054 g, 1 mmol). The abovementioned solution is stirred under room temperature, and 20 mL of tetrahydrofuran solution contained the compound No. 31 (0.1 g, 0.35 mmol) is dropped thereinto. The mixture is then treated by a reverse flow for 2 hours. After drying the mixture, the precipitate is collected and washed by cold alcohol, so as to obtain the compound No. 41.

The compound No. 41 has the following characteristics: Mol. Wt.: 414.0151; Melting Point (° C.): 285.1.

Embodiment 40 (4-Chloro-3-(3,5-dimethylbenzenethio)9H-thioxanthen-9-one 10,10-dioxide, No. 42)

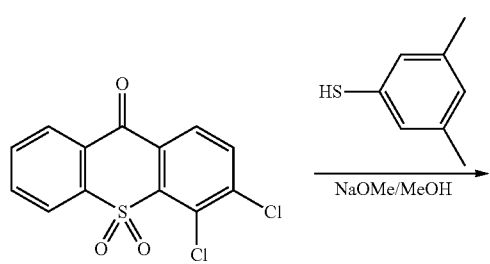

3,5-dimethylbenzenethiol (1 mmol) with appropriate amount is slowly dropped into 10 mL of methanol contained sodium methoxide (0.054 g, 1 mmol). The abovementioned solution is stirred under room temperature, and 20 mL of tetrahydrofuran solution contained the compound No. 31 (0.1 g, 0.35 mmol) is dropped thereinto. The mixture is then treated by a reverse flow for 2 hours. After drying the mixture, the precipitate is collected and washed by cold alcohol, so as to obtain the compound No. 42.

The compound No. 42 has the following characteristics: Mol. Wt.: 414.0151; Melting Point (° C.): 275.3.

Embodiment 41 (4-Chloro-3-(3-methylbenzenethio)9H-thioxanthen-9-one 10,10-dioxide, No. 43)

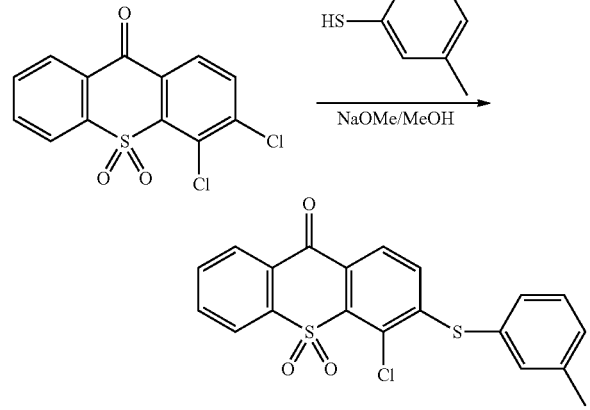

3-Methylbenzenethiol (1 mmol) with appropriate amount is slowly dropped into 10 mL of methanol contained sodium methoxide (0.054 g, 1 mmol). The abovementioned solution is stirred under room temperature, and 20 mL of tetrahydrofuran solution contained the compound No. 31 (0.1 g, 0.35 mmol) is dropped thereinto. The mixture is then treated by a reverse flow for 2 hours. After drying the mixture, the precipitate is collected and washed by cold alcohol, so as to obtain the compound No. 43.

The compound No. 43 has the following characteristics: Mol. Wt.: 399.9995; Melting Point (° C.): 248.

Embodiment 42 (4-Chloro-3-((4-chlorophenyl)methanethio)9H-thioxanthen-9-one 10,10-dioxide, No. 44)

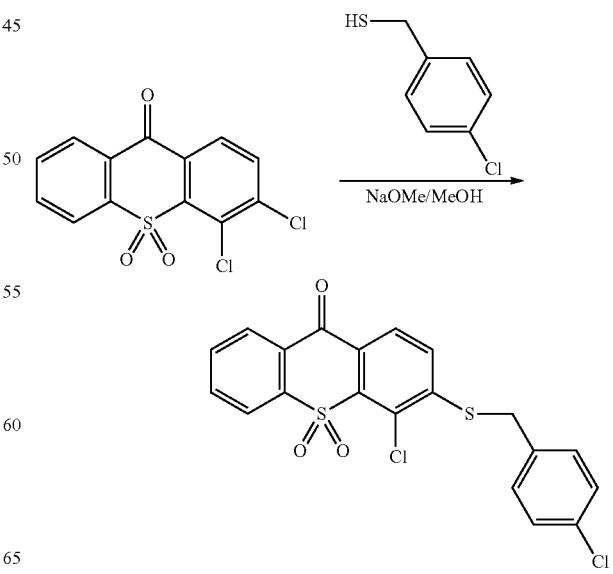

(4-chlorophenyl)methanethiol (1 mmol) with appropriate amount is slowly dropped into 10 mL of methanol contained sodium methoxide (0.054 g, 1 mmol). The above-mentioned solution is stirred under room temperature, and 20 mL of tetrahydrofuran solution contained the compound No. 31 (0.1 g, 0.35 mmol) is dropped thereinto. The mixture is then treated by a reverse flow for 2 hours. After drying the mixture, the precipitate is collected and washed by cold alcohol, so as to obtain the compound No. 44.

The compound No. 44 has the following characteristics: Mol. Wt.: 433.9605; Melting Point (° C.): 256.5; 13C-NMR (75 MHz, CDCl$_3$), δ(ppm): 36.32, 124.05, 128.18, 128.83, 129.51, 130.39, 133.30, 135.41, 176.99.

Embodiment 43 (4-Chloro-3-(3-ethoxybenzenethio) 9H-thioxanthen-9-one 10,10-dioxide, No. 45)

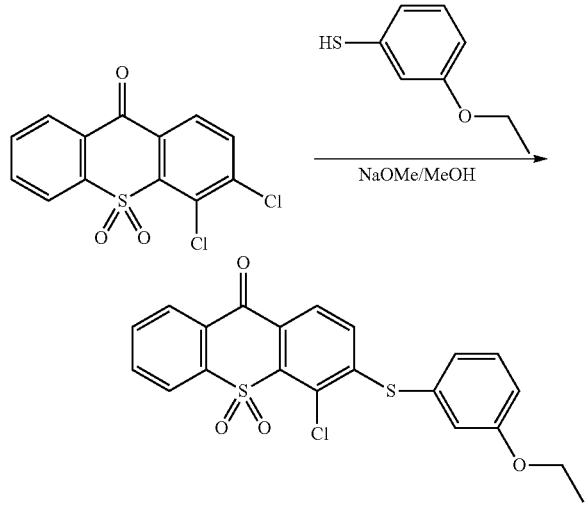

3-ethoxybenzenethiol (1 mmol) with appropriate amount is slowly dropped into 10 mL of methanol contained sodium methoxide (0.054 g, 1 mmol). The abovementioned solution is stirred under room temperature, and 20 mL of tetrahydrofuran solution contained the compound No. 31 (0.1 g, 0.35 mmol) is dropped thereinto. The mixture is then treated by a reverse flow for 2 hours. After drying the mixture, the precipitate is collected and washed by cold alcohol, so as to obtain the compound No. 45.

The compound No. 45 has the following characteristics: Mol. Wt.: 430.0100; Melting Point (° C.): 227; 1H-NMR (300 MHz, CDCl$_3$), δ(ppm): 1.43 (d, J=6.9 Hz, 3H, CH$_3$), 4.05 (q, J=6.9 Hz, 1H, CH$_2$), 7.00 (d, J=8.7 Hz, 1H, Ar—H), 7.05-7.11 (m, 2H, Ar—H), 7.16 (d, J=7.2 Hz, 1H, Ar—H), 7.43 (t, J=8.1 Hz, Ar—H), 7.78 (td, J=7.8 Hz, 1.2 Hz, 1H, Ar—H), 7.91 (td, J=7.8 Hz, 1.2 Hz, 1H, Ar—H), 8.09 (d, J=8.7 Hz, 1H, Ar—H), 8.18 (dd, J=7.8 Hz, 1H, Ar—H), 8.32 (dd, J=7.8 Hz, 0.9 Hz, 1H, Ar—H); 13C-NMR (75 MHz, CDCl$_3$), δ(ppm): 14.71, 64.11, 117.61, 121.54, 124.02, 126.75, 127.99, 128.50, 128.79, 129.27, 129.56, 129.88, 131.51, 133.23, 135.31, 138.55, 142.85, 151.58, 160.72, 162.01, 177.02 (CO).

Embodiment 44 (4-Chloro-3-(4-isopropylbenzenethio)9H-thioxanthen-9-one 10,10-dioxide, No. 46)

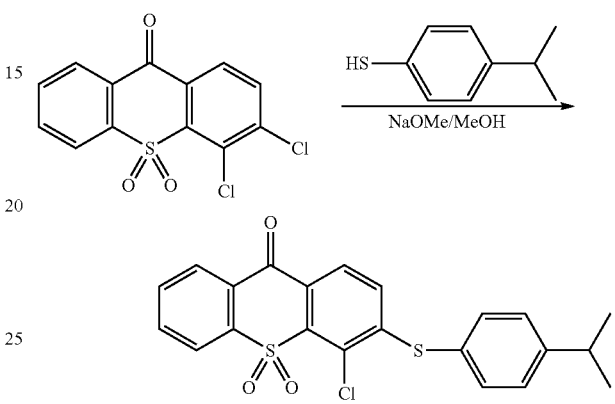

4-isopropylbenzenethiol (1 mmol) with appropriate amount is slowly dropped into 10 mL of methanol contained sodium methoxide (0.054 g, 1 mmol). The abovementioned solution is stirred under room temperature, and 20 mL of tetrahydrofuran solution contained the compound No. 31 (0.1 g, 0.35 mmol) is dropped thereinto. The mixture is then treated by a reverse flow for 2 hours. After drying the mixture, the precipitate is collected and washed by cold alcohol, so as to obtain the compound No. 46.

The compound No. 46 has the following characteristics: Mol. Wt.: 428.0308; Melting Point (° C.): 265; 1H-NMR (300 MHz, CDCl$_3$), δ(ppm): 1.31 (d, J=7.2 Hz, 6H, (CH$_3$)$_2$), 3.00 (q, J=7.2 Hz, 1H, CH), 6.96 (d, J=8.7 Hz, 1H, Ar—H), 7.39 (dd, J=8.4 Hz, 2.1H, Ar—H), 7.50 (d, J=8.1 Hz, 2.1H, Ar—H), 7.78 (td, J=7.8 Hz, 1.2 Hz, 1H, Ar—H), 7.91 (td, J=7.8 Hz, 1.2 Hz, 1H, Ar—H), 8.09 (d, J=8.7 Hz, 1H, Ar—H), 8.18 (dd, J=8.1 Hz, 1.2 Hz, 1H, Ar—H), 8.32 (dd, J=7.8 Hz, 1.2 Hz, 1H, Ar—H); 13C-NMR (75 MHz, CDCl$_3$), δ(ppm): 23.82 (CH$_3$), 34.18 (CH), 124.02, 125.63, 127.95, 128.36, 128.77, 128.97, 129.30, 133.20, 135.28, 136.25, 142.89, 152.12, 152.33, 177.04 (CO).

Embodiment 45 (4-Chloro-3-(4-bromobenzenethio) 9H-thioxanthen-9-one 10,10-dioxide, No. 47)

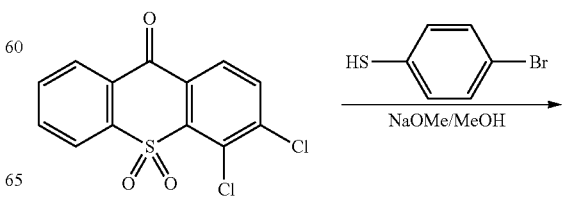

-continued

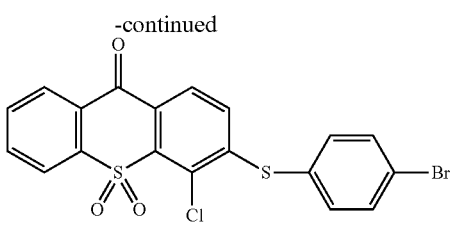

4-bromobenzenethiol (1 mmol) with appropriate amount is slowly dropped into 10 mL of methanol contained sodium methoxide (0.054 g, 1 mmol). The abovementioned solution is stirred under room temperature, and 20 mL of tetrahydrofuran solution contained the compound No. 31 (0.1 g, 0.35 mmol) is dropped thereinto. The mixture is then treated by a reverse flow for 2 hours. After drying the mixture, the precipitate is collected and washed by cold alcohol, so as to obtain the compound No. 47.

The compound No. 47 has the following characteristics: Mol. Wt.: 463.8943; Melting Point (° C.): 257; 1H-NMR (300 MHz, CDCl$_3$), δ(ppm): 6.97 (d, J=8.7 Hz, 1H, Ar—H), 7.46 (d, J=8.1 Hz, 1H, Ar—H), 7.67 (d, J=8.1 Hz, 1H, Ar—H), 7.79 (t, J=7.5 Hz, 1H, Ar—H), 7.92 (t, J=7.5 Hz, 1H, Ar—H), 8.11 (d, J=8.7 Hz, 1H, Ar—H), 8.18 (d, J=7.8 Hz, 1H, Ar—H), 8.33 (d, J=7.8 Hz, 1H, Ar—H); 13C-NMR (75 MHz, CDCl$_3$), δ(ppm): 123.25, 124.98, 127.34, 128.06, 128.42, 128.68, 132.52, 133.28, 134.62, 136.70, 142.01, 149.73, 176.16.

Embodiment 46 (3-(benzylthio)-4-chloro-9H-thioxanthen-9-one 10,10-dioxide, No. 48)

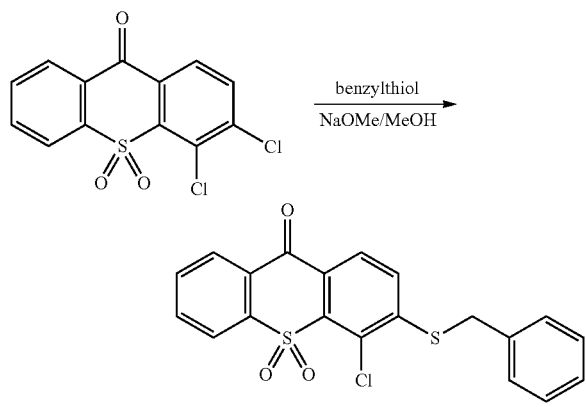

Benzylthiol (1 mmol) with appropriate amount is slowly dropped into 10 mL of methanol contained sodium methoxide (0.054 g, 1 mmol). The abovementioned solution is stirred under room temperature, and 20 mL of tetrahydrofuran solution contained the compound No. 31 (0.1 g, 0.35 mmol) is dropped thereinto. The mixture is then treated by a reverse flow for 2 hours. After drying the mixture, the precipitate is collected and washed by cold alcohol, so as to obtain the compound No. 48.

The compound No. 48 has the following characteristics: Mol. Wt.: 399.9995 (C$_{20}$H$_{13}$ClO$_3$S$_2$); Melting Point (° C.): 215; 1H-NMR (300 MHz, CDCl$_3$), δ(ppm): 4.30 (s, 2H, CH$_2$), 7.31-7.45 (m, 6H, Ar—H), 7.52 (d, J=8.4 Hz, 1H, Ar—H), 7.78 (td, J=7.5 Hz, 1.2 Hz, 1H, Ar—H), 7.91 (td, J=7.5 Hz, 1.2 Hz, 1H, Ar—H), 8.17 (d, J=7.8 Hz, 1H, Ar—H), 8.24 (d, J=8.7 Hz, 1H, Ar—H), 8.34 (dd, J=8.7 Hz, 0.9 Hz, 1H, Ar—H).

Embodiment 47 (4-chloro-3-(2-isopropylphenylthio)-9H-thioxanthen-9-one 10,10-dioxide, No. 49)

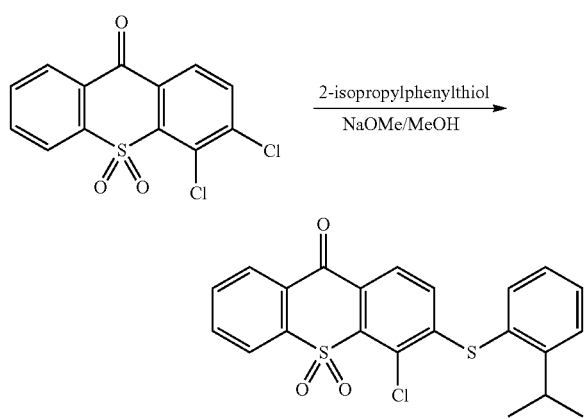

2-Isopropylphenylthiol (1 mmol) with appropriate amount is slowly dropped into 10 mL of methanol contained sodium methoxide (0.054 g, 1 mmol). The abovementioned solution is stirred under room temperature, and 20 mL of tetrahydrofuran solution contained the compound No. 31 (0.1 g, 0.35 mmol) is dropped thereinto. The mixture is then treated by a reverse flow for 2 hours. After drying the mixture, the precipitate is collected and washed by cold alcohol, so as to obtain the compound No. 49.

The compound No. 49 has the following characteristics: Mol. Wt.: 428.0308 (C$_{22}$H$_{17}$ClO$_3$S$_2$); Melting Point (° C.): 227; 1H-NMR (300 MHz, CDCl$_3$), δ(ppm): 1.20 (d, J=7.2 Hz, 6H, (CH$_3$)$_2$), 3.39 (t, J=7.2 Hz, 1H, CH), 6.78 (d, J=8.7 Hz, 1H, Ar—H), 7.30-7.35 (m, 1H, Ar—H), 7.55 (d, J=8.7 Hz, 3H, Ar—H), 7.78 (td, J=7.5 Hz, 1.2 Hz, 1H, Ar—H), 7.91 (td, J=7.5 Hz, 1.2 Hz, 1H, Ar—H), 8.07 (d, J=8.4 Hz, 1H, Ar—H), 8.19 (dd, J=8.1 Hz, 0.9 Hz, 1H, Ar—H), 8.32 (dd, J=8.1 Hz, 0.9 Hz, 1H, Ar—H); 13C-NMR (75 MHz, CDCl$_3$), δ(ppm): 23.11, 30.52, 123.23, 125.85, 126.19, 126.94, 127.15, 127.24, 127.49, 128.00, 128.17, 128.52, 131.16, 132.45, 134.50, 136.94, 137.75, 142.05, 151.09, 153.37, 176.23.

Embodiment 48 (4-chloro-3-(propylthio)-9H-thioxanthen-9-one 10,10-dioxide, No. 50)

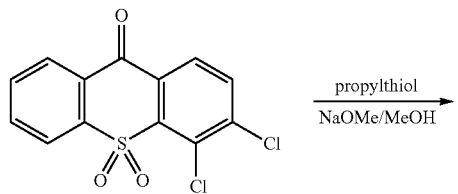

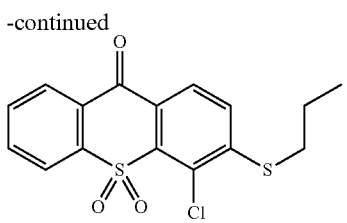

Propylthiol (1 mmol) with appropriate amount is slowly dropped into 10 mL of methanol contained sodium methoxide (0.054 g, 1 mmol). The abovementioned solution is stirred under room temperature, and 20 mL of tetrahydrofuran solution contained the compound No. 31 (0.1 g, 0.35 mmol) is dropped thereinto. The mixture is then treated by a reverse flow for 2 hours. After drying the mixture, the precipitate is collected and washed by cold alcohol, so as to obtain the compound No. 50.

The compound No. 50 has the following characteristics: Mol. Wt.: 351.9995; Melting Point (° C.): 273.

Embodiment 49 (4-chloro-3-(4-methoxyphenylthio)-9H-thioxanthen-9-one 10,10-dioxide, No. 51)

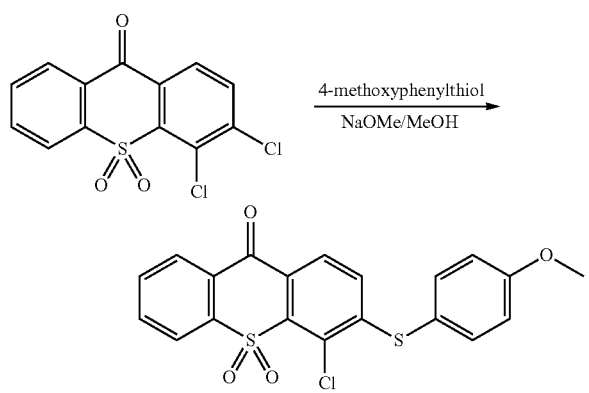

4-Methoxyphenylthiol (1 mmol) with appropriate amount is slowly dropped into 10 mL of methanol contained sodium methoxide (0.054 g, 1 mmol). The abovementioned solution is stirred under room temperature, and 20 mL of tetrahydrofuran solution contained the compound No. 31 (0.1 g, 0.35 mmol) is dropped thereinto. The mixture is then treated by a reverse flow for 2 hours. After drying the mixture, the precipitate is collected and washed by cold alcohol, so as to obtain the compound No. 51.

The compound No. 51 has the following characteristics: Mol. Wt.: 415.9944 ($C_{20}H_{13}ClO_4S_2$); Melting Point (° C.): 264; 1H-NMR (300 MHz, CDCl$_3$), δ(ppm): 6.92 (d, J=8.7 Hz, 1H, Ar—H), 7.05 (td, J=8.7 Hz, 2.1 Hz, 2H, Ar—H), 7.50 (td, J=8.7 Hz, 2.1 Hz, 2H, Ar—H), 7.77 (td, J=7.5 Hz, 1.2 Hz, 1H, Ar—H), 7.91 (td, J=7.5 Hz, 1.2 Hz, 1H, Ar—H), 8.08 (d, J=8.7 Hz, 1H, Ar—H), 8.18 (dd, J=8.1 Hz, 0.9 Hz, 1H, Ar—H), 8.32 (dd, J=8.1 Hz, 0.9 Hz, 1H, Ar—H); 13C-NMR (75 MHz, CDCl$_3$), δ(ppm): 55.67, 116.45, 119.12, 124.01, 126.38, 127.91, 128.30, 128.78, 129.01, 129.30, 133.21, 135.28, 137.98, 138.50, 142.88, 152.60, 162.13, 177.05.

Embodiment 50 (4-chloro-3-(2,3-dichlorophenylthio)-9H-thioxanthen-9-one 10,10-dioxide, No. 52)

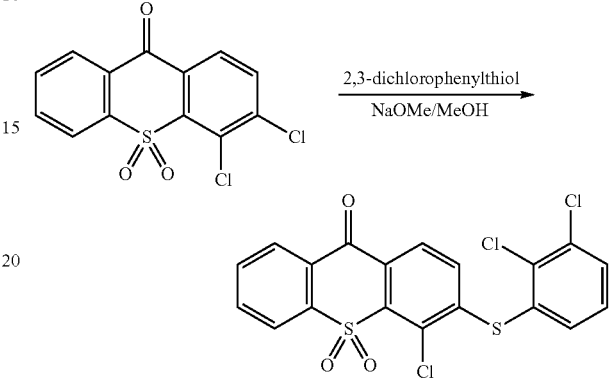

2,3-dichlorophenylthiol (1 mmol) with appropriate amount is slowly dropped into 10 mL of methanol contained sodium methoxide (0.054 g, 1 mmol). The abovementioned solution is stirred under room temperature, and 20 mL of tetrahydrofuran solution contained the compound No. 31 (0.1 g, 0.35 mmol) is dropped thereinto. The mixture is then treated by a reverse flow for 2 hours. After drying the mixture, the precipitate is collected and washed by cold alcohol, so as to obtain the compound No. 52.

The compound No. 52 has the following characteristics: Mol. Wt.: 453.9059 ($C_{19}H_9Cl_3O_3S_2$); Melting Point (° C.): 283; 1H-NMR (300 MHz, CDCl$_3$), δ(ppm): 6.91 (d, J=8.4 Hz, 1H), 7.35 (t, J=7.8 Hz, 1H), 7.61 (d, J=7.2 Hz, 1H), 7.67 (d, J=7.5 Hz, 1H), 7.79 (t, J=7.5 Hz, 1H), 7.92 (d, J=7.5 Hz, 1H), 8.17 (d, J=3 Hz, 1H), 8.33 (d, J=7.2 Hz, 1H).

Embodiment 51 (4-chloro-3-(2,5-dimethylphenylthio)-9H-thioxanthen-9-one 10,10-dioxide, No. 53)

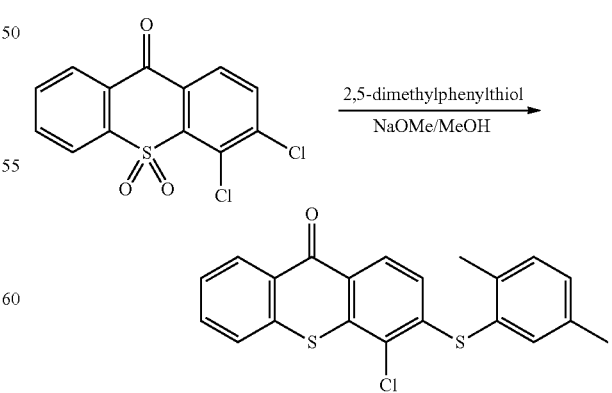

2,5-dimethylphenylthiol (1 mmol) with appropriate amount is slowly dropped into 10 mL of methanol contained sodium methoxide (0.054 g, 1 mmol). The abovementioned solution is stirred under room temperature, and 20 mL of tetrahydrofuran solution contained the compound No. 31 (0.1 g, 0.35 mmol) is dropped thereinto. The mixture is then treated by a reverse flow for 2 hours. After drying the mixture, the precipitate is collected and washed by cold alcohol, so as to obtain the compound No. 53.

The compound No. 53 has the following characteristics: Mol. Wt.: 414.0151; Melting Point (° C.): 239; 1H-NMR (300 MHz, CDCl$_3$), δ(ppm): 6.78 (d, J=8.7 Hz, 1H, Ar—H), 7.31 (t, J=7.8 Hz, 2H, Ar—H), 7.40 (s, 1H, Ar—H), 7.78 (td, J=7.5 Hz, 1.2 Hz, 1H, Ar—H), 7.91 (td, J=7.5 Hz, 1.2 Hz, 1H, Ar—H), 8.07 (d, J=8.7 Hz, 1H, Ar—H), 8.18 (d, J=7.8 Hz, 1H, Ar—H), 8.32 (dd, J=8.0 Hz, 1.2 Hz, 1H, Ar—H); 13C-NMR (75 MHz, CDCl$_3$), δ(ppm): 20.04, 20.73, 124.01, 126.79, 127.64, 128.01, 128.27, 128.70, 128.77, 129.30, 131.78, 132.36, 133.22, 135.29, 137.80, 138.09, 138.59, 140.48, 142.84, 151.05, 177.04.

Embodiment 52 (3-(3-aminophenylthio)-4-chloro-9H-thioxanthen-9-one 10,10-dioxide, No. 54)

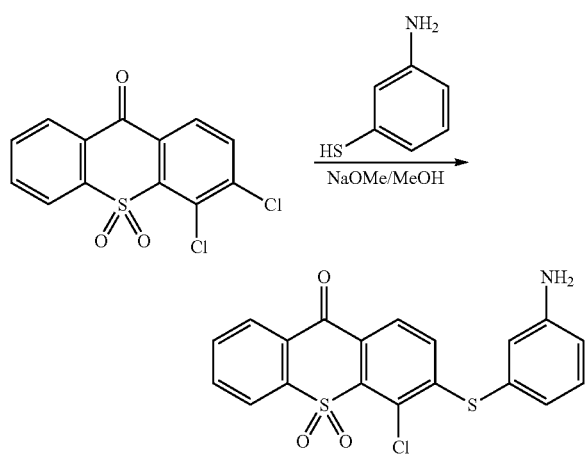

3-aminophenylthiol (1 mmol) with appropriate amount is slowly dropped into 10 mL of methanol contained sodium methoxide (0.054 g, 1 mmol). The abovementioned solution is stirred under room temperature, and 20 mL of tetrahydrofuran solution contained the compound No. 31 (0.1 g, 0.35 mmol) is dropped thereinto. The mixture is then treated by a reverse flow for 2 hours. After drying the mixture, the precipitate is collected and washed by cold alcohol, so as to obtain the compound No. 54.

The compound No. 54 has the following characteristics: Mol. Wt.: 400.9947 (C$_{19}$H$_{12}$ClNO$_3$S$_2$); Melting Point (° C.): 237.

Embodiment 53 (4-chloro-3-(3-methoxyphenylthio)-9H-thioxanthen-9-one 10,10-dioxide, No. 55)

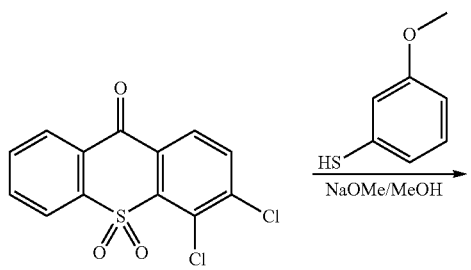

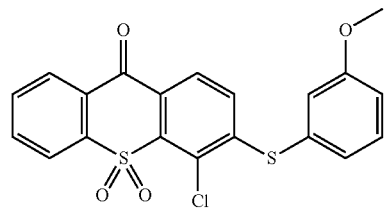

3-methoxyphenylthiol (1 mmol) with appropriate amount is slowly dropped into 10 mL of methanol contained sodium methoxide (0.054 g, 1 mmol). The abovementioned solution is stirred under room temperature, and 20 mL of tetrahydrofuran solution contained the compound No. 31 (0.1 g, 0.35 mmol) is dropped thereinto. The mixture is then treated by a reverse flow for 2 hours. After drying the mixture, the precipitate is collected and washed by cold alcohol, so as to obtain the compound No. 55.

The compound No. 55 has the following characteristics: Mol. Wt.: 415.9944 (C$_{20}$H$_{13}$ClO$_4$S$_2$); Melting Point (° C.): 232☐; 1H-NMR (300 MHz, CDCl$_3$), δ(ppm): 7.00 (d, J=8.4 Hz, 1H, Ar—H), 7.07-7.11 (m, 2H, Ar—H), 7.71 (d, J=7.5 Hz, 1H, Ar—H), 7.44 (t, J=7.8 Hz, 1H, Ar—H), 7.77 (t, J=7.5 Hz, 1H, Ar—H), 7.91 (t, J=7.5 Hz, 1H, Ar—H), 8.09 (d, J=8.4 Hz, 1H, Ar—H), 8.18 (d, J=8.1 Hz, 1H, Ar—H), 8.32 (d, J=7.5 Hz, 1H, Ar—H); 13C-NMR (75 MHz, CDCl$_3$), δ(ppm): 55.70, 117.06, 120.93, 124.02, 126.77, 128.01, 128.17, 128.54, 128.80, 129.27, 129.55, 130.01, 131.54, 133.24, 135.32, 138.57, 142.85, 151.49, 161.37, 177.01.

Embodiment 54 (4-chloro-3-(2-methoxyphenylthio)-9H-thioxanthen-9-one 10,10-dioxide, No. 56)

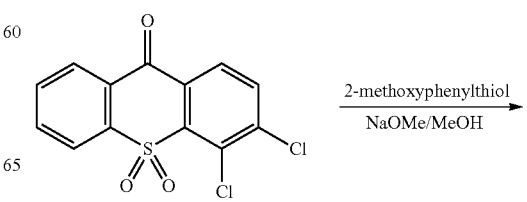

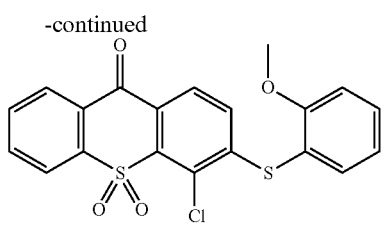

2-methoxyphenylthiol (1 mmol) with appropriate amount is slowly dropped into 10 mL of methanol contained sodium methoxide (0.054 g, 1 mmol). The abovementioned solution is stirred under room temperature, and 20 mL of tetrahydrofuran solution contained the compound No. 31 (0.1 g, 0.35 mmol) is dropped thereinto. The mixture is then treated by a reverse flow for 2 hours. After drying the mixture, the precipitate is collected and washed by cold alcohol, so as to obtain the compound No. 56.

The compound No. 56 has the following characteristics: Mol. Wt.: 415.9944 ($C_{20}H_{13}ClO_4S_2$); Melting Point (° C.): 275; 1H-NMR (300 MHz, $CDCl_3$), δ(ppm): 3.82 (s, 3H, 2-OMe), 6.87 (d, J=8.4 Hz, 1H), 7.05-7.11 (m, 2H), 7.53-7.59 (m, 2H), 7.77 (t, J=7.5 Hz, 1H), 7.90 (t, J=7.5 Hz, 1H), 8.06 (d, J=8.4 Hz, 1H), 8.18 (d, J=7.8 Hz, 1H), 8.32 (d, J=7.8 Hz, 1H) 13C-NMR (75 MHz, $CDCl_3$), δ(ppm): 56.21, 112.51, 116.77, 122.31, 124.30, 126.94, 127.66, 128.37, 128.75, 129.17, 129.44, 133.14, 135.21, 137.97, 138.57, 143.04, 150.67, 160.75, 177.17.

Embodiment 55 (4-chloro-3-(2-chlorobenzylthio)-9H-thioxanthen-9-one 10,10-dioxide, No. 57)

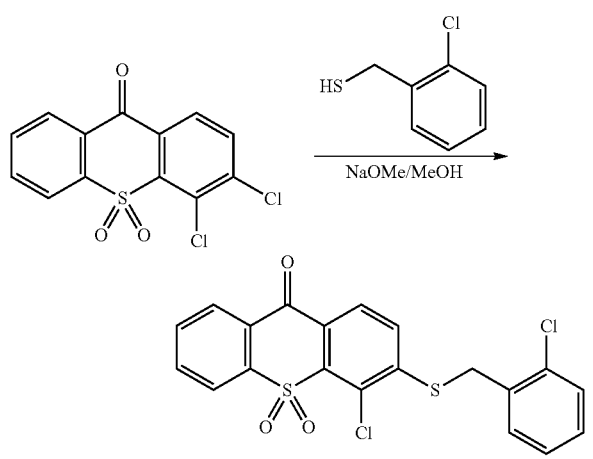

2-chlorobenzylthiol (1 mmol) with appropriate amount is slowly dropped into 10 mL of methanol contained sodium methoxide (0.054 g, 1 mmol). The abovementioned solution is stirred under room temperature, and 20 mL of tetrahydrofuran solution contained the compound No. 31 (0.1 g, 0.35 mmol) is dropped thereinto. The mixture is then treated by a reverse flow for 2 hours. After drying the mixture, the precipitate is collected and washed by cold alcohol, so as to obtain the compound No. 57.

The compound No. 57 has the following characteristics: Mol. Wt.: 433.9605; Melting Point (° C.): 256; 1H-NMR (300 MHz, $CDCl_3$), δ(ppm): 4.40 (s, 2H), 7.27-7.30 (m, 2H), 7.43-7.52 (m, 3H), 7.77 (t, J=8.1 Hz, 1.2 Hz, 1H), 7.90 (t, J=8.1 Hz, 1.2 Hz, 1H), 8.06 (dd, J=8.1 Hz, 0.9 Hz, 1H), 8.27 (d, J=8.4 Hz, 1H), 8.35 (dd, J=8.1 Hz, 1.2 Hz, 1H); 13C-NMR (75 MHz, $CDCl_3$), δ(ppm): 34.37, 99.16, 123.90, 127.53, 128.08, 128.67, 129.65, 130.14, 130.68, 133.12, 134.55, 135.22, 176.88.

Embodiment 56 (4-chloro-3-(4-nitrophenylthio)-9H-thioxanthen-9-one 10,10-dioxide, No. 58)

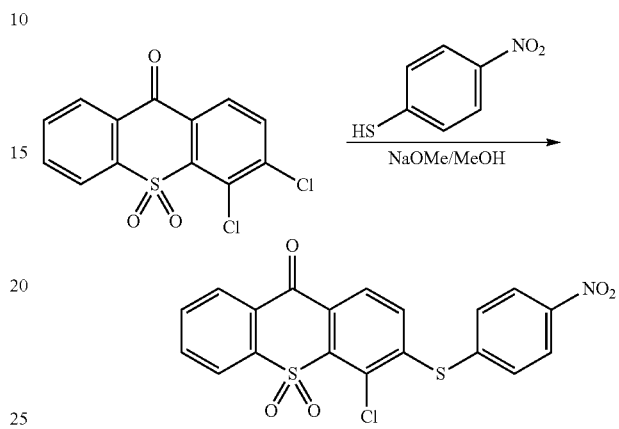

4-nitrophenylthiol (1 mmol) with appropriate amount is slowly dropped into 10 mL of methanol contained sodium methoxide (0.054 g, 1 mmol). The abovementioned solution is stirred under room temperature, and 20 mL of tetrahydrofuran solution contained the compound No. 31 (0.1 g, 0.35 mmol) is dropped thereinto. The mixture is then treated by a reverse flow for 2 hours. After drying the mixture, the precipitate is collected and washed by cold alcohol, so as to obtain the compound No. 58.

The compound No. 58 has the following characteristics: Mol. Wt.: 430.9689; Melting Point (° C.): 249; 1H-NMR (300 MHz, $CDCl_3$), δ(ppm): 7.22 (d, J=8.7 Hz, 1H, Ar—H), 7.61 (dd, J=9 Hz, 2.1 Hz, 1H, Ar—H), 7.69 (td, J=9 Hz, 2.1 Hz, 2H, Ar—H), 7.80 (td, J=7.8 Hz, 1.2 Hz, 1H, Ar—H), 7.93 (td, J=7.8 Hz, 1.2 Hz, 1H, Ar—H), 8.17-8.20 (m, 2H, Ar—H), 8.29-8.35 (m, 2H, Ar—H); 13C-NMR (75 MHz, $CDCl_3$), δ(ppm): 123.33, 123.90, 124.54, 126.13, 127.64, 128.17, 128.32, 129.44, 131.05, 132.66, 133.86, 134.83, 138.41, 141.98, 143.59, 146.42, 148.14, 176.07.

The present invention further provides a pharmaceutical composition for inhibiting tumor growth, comprising a thioxanthone ring system derivative compound with an effective amount and a pharmaceutically acceptable excipient, wherein the thioxanthone ring system derivative compound being represented by a formula (I).

The abovementioned pharmaceutical composition can inhibit tumor growth for treating cancer. The tumor includes a solid tumor or a non-solid tumor. The cancer caused by the solid tumor comprises lung cancer, colorectal cancer, central nervous system cancer, melanoma, ovarian cancer, prostate cancer, kidney cancer, breast cancer, small cell cervical cancer, gastric cancer, cervical cancer, osteosarcoma . . . etc. The cancer caused by the non-solid tumor comprises is Leukemia, lymphoma cancer, multiple myeloma . . . etc.

The excipient comprises but not limit to a diluent, a filler, a binder, a disintegrant, a lubricant. Furthermore, the excipient comprises but not limit of microcrystalline cellulose, polyvinyl pyrrolidone, corn starch, modified starches, sodium starch glycolate, resin, gelatinized starches, carbohydrate, polyethylene glycol, polyvinyl alcohol, hydroxypropyl cellulose, methylcellulose, hydroxymethyl cellulose, hydroxypropyl methylcellulose.

In order to prove that the compound No. 1~59 contained the thioxanthone ring system derivative represented by formula (I) can effectively treat cancer, the compounds No. 1~58 manufactured by the method discloses in the present invention will process a series of pharmacological activities tests.

Figure 4A:
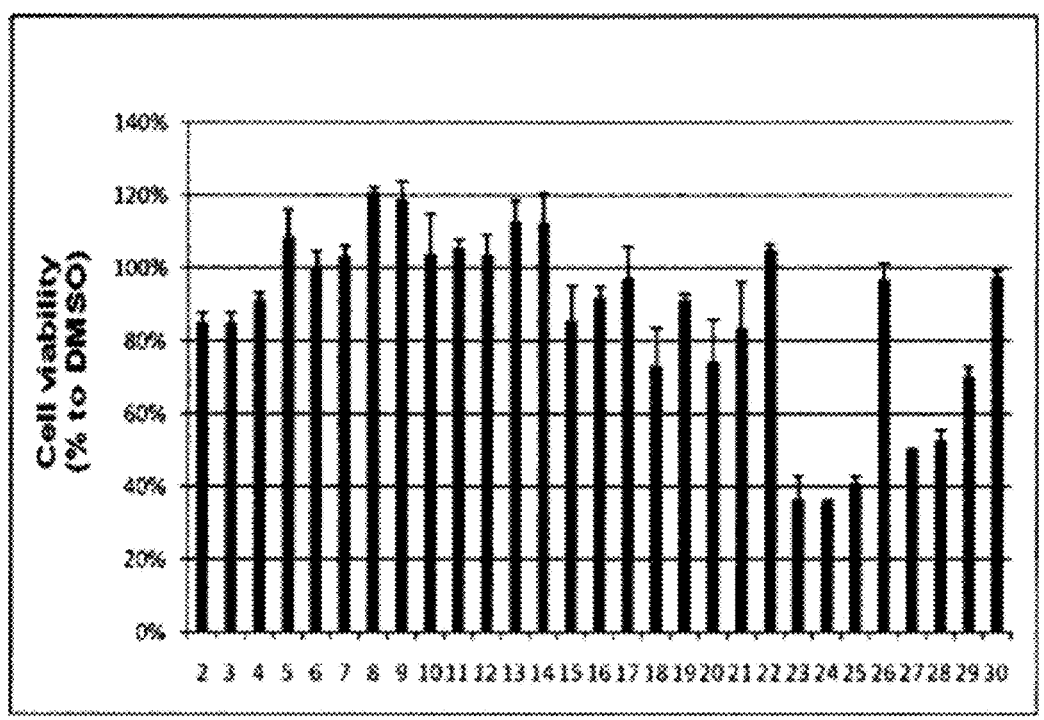
FIG. 4A is a diagram showing the cell viabilities of A control cell lines by using the compounds No. 2~30.
Figure 4B:
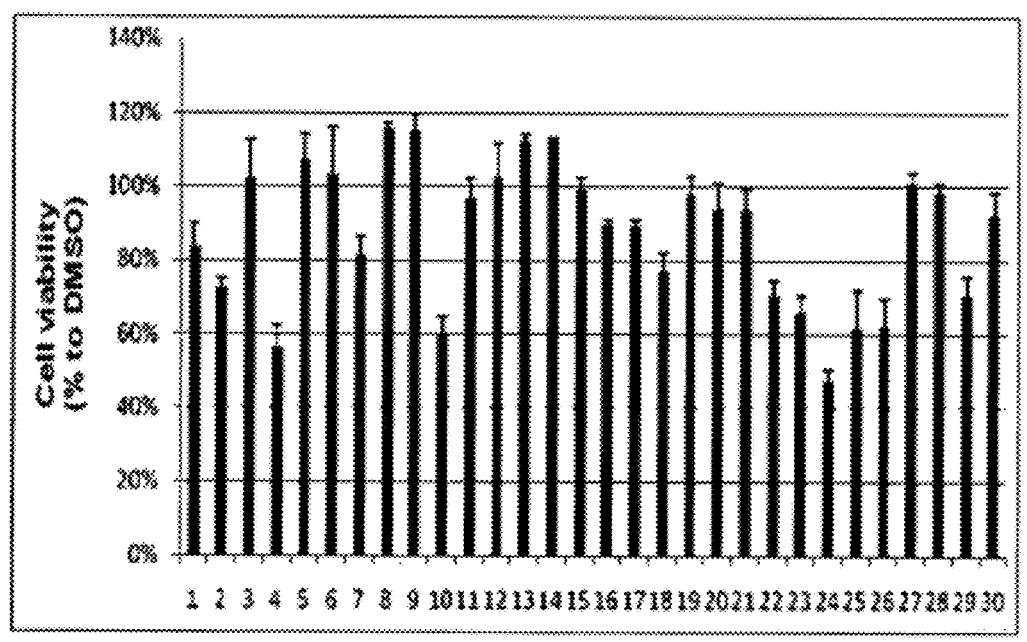
FIG. 4B is a diagram showing the cell viabilities of A3 cell lines by using the compounds No. 1~30.
Figure 4C:
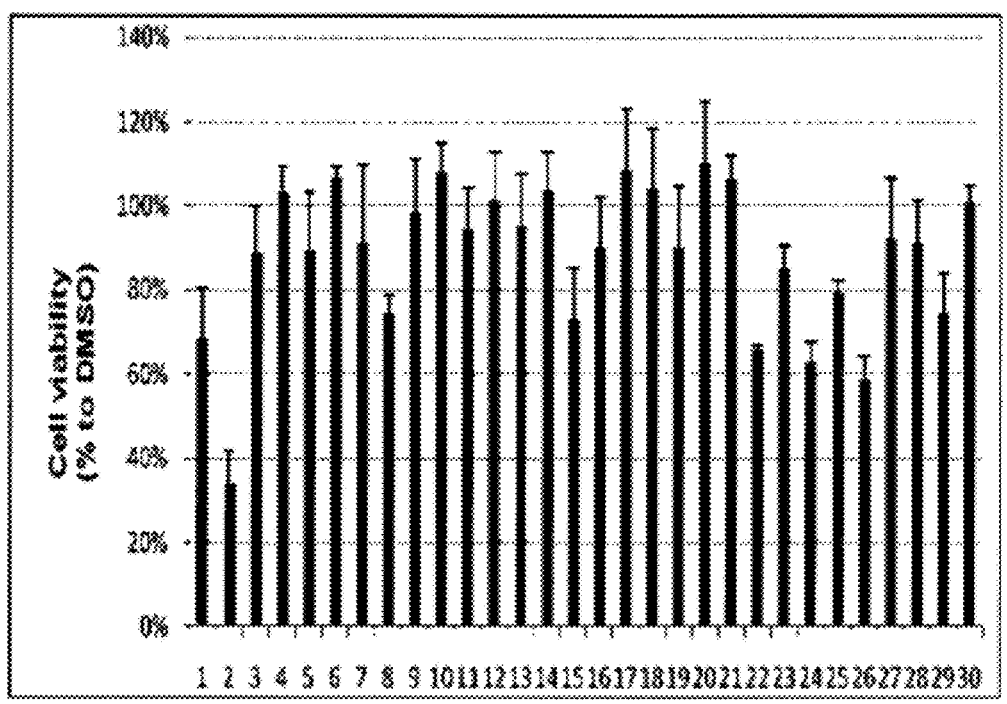
FIG. 4C is a diagram showing the cell viabilities of HEL299 fibroblast by using the compounds No. 1~30.

Please refer to Table 1 and FIGS. 4A-4C. According to a MTT assay (Table 1), various cell viabilities of the A control cell lines can be obtained and illustrated in FIG. 4A while the compounds No. 2~30 are used to treat A control cell lines, wherein A control cell lines are lung cancer cell. And then, the compounds having the better inhibition effect on cancer cell are the compound No. 23 (36.6%), the compound No. 24 (35.5%), the compound No. 25 (40.8%), the compound No. 27 (50.5%) and the compound No. 28 (52.9%).

TABLE 1

MTT assay

| | A control | A3 | HEL299 |
|---|---|---|---|
| 1 | none | 83.7 ± 6.22 | 68.5 ± 12.0 |
| 2 | 85.1 ± 2.74 | 72.7 ± 2.60 | 34.0 ± 7.95 |
| 3 | 84.8 ± 2.95 | 103 ± 10.2 | 88.9 ± 11.1 |
| 4 | 91.1 ± 2.02 | 56.1 ± 6.42 | 103 ± 6.21 |
| 5 | 108 ± 7.69 | 107 ± 7.17 | 89.5 ± 13.7 |
| 6 | 99.7 ± 4.76 | 103 ± 13.0 | 107 ± 2.62 |
| 7 | 103 ± 2.86 | 81.6 ± 4.98 | 91.1 ± 18.7 |
| 8 | 120 ± 1.51 | 116 ± 1.49 | 74.8 ± 4.04 |
| 9 | 119 ± 4.69 | 115 ± 4.55 | 98.4 ± 12.8 |
| 10 | 104 ± 11.0 | 59.9 ± 4.83 | 108 ± 7.19 |
| 11 | 105 ± 2.56 | 96.9 ± 5.20 | 94.4 ± 10.1 |
| 12 | 103 ± 5.86 | 102 ± 9.52 | 101 ± 9.52 |
| 13 | 113 ± 5.86 | 112 ± 1.86 | 112 ± 11.2 |
| 14 | 112 ± 8.03 | 113 ± 0.50 | 104 ± 9.21 |
| 15 | 85.4 ± 9.66 | 99.0 ± 3.41 | 73.0 ± 12.3 |
| 16 | 91.8 ± 3.07 | 90.0 ± 1.24 | 90.6 ± 11.5 |
| 17 | 97.1 ± 8.74 | 89.4 ± 1.88 | 109 ± 14.5 |
| 18 | 73.2 ± 10.2 | 77.2 ± 5.23 | 104 ± 14.2 |
| 19 | 91.3 ± 1.74 | 98.2 ± 4.79 | 90.3 ± 14.4 |
| 20 | 74.6 ± 11.2 | 93.9 ± 6.97 | 110 ± 14.3 |
| 21 | 83.5 ± 12.6 | 93.7 ± 6.01 | 107 ± 5.40 |
| 22 | 104 ± 1.89 | 70.8 ± 3.86 | 66.1 ± 0.66 |
| 23 | 36.6 ± 6.15 | 65.9 ± 4.49 | 85.2 ± 5.26 |
| 24 | 35.5 ± 0.86 | 47.8 ± 2.62 | 62.7 ± 4.89 |
| 25 | 40.8 ± 1.90 | 61.5 ± 10.3 | 79.3 ± 30.2 |
| 26 | 96.8 ± 4.29 | 62.4 ± 7.31 | 58.7 ± 5.55 |
| 27 | 50.5 ± 0.08 | 101 ± 2.95 | 92.4 ± 14.4 |
| 28 | 52.9 ± 2.79 | 98.3 ± 2.25 | 91.2 ± 10.4 |
| 29 | 70.1 ± 2.68 | 70.3 ± 5.31 | 74.5 ± 9.39 |
| 30 | 97.7 ± 1.46 | 92.2 ± 6.17 | 101 ± 3.70 |

Please to FIG. 4B, various cell viabilities of the A3 cell lines can be obtained through the MTT assay and illustrated in FIG. 4B while the compounds No. 1~30 are used to treat A3 cell lines, wherein A3 cell lines are lung cancer stem cell. And then, the compounds having the better inhibition effect on cancer cell are the compound No. 4 (56.1%), the compound No. 10 (59.9%), the compound No. 23 (65.9%), the compound No. 24 (47.8%), the compound No. 25 (61.5%) and the compound No. 26 (62.4%).

Please refer to FIG. 4C, various cell viabilities of the HEL299 cell lines can be obtained through the MTT assay while the compounds No. 1~30 are used to treat HEL299 cell lines, wherein HEL299 cell lines are fibroblast. And then, the compounds having no inhibition effect on normal cell are the compound No. 4 (103%), the compound No. 10 (108%), the compound No. 23 (82.5%), the compound No. 25 (79.3%), the compound No. 27 (92.4%) and the compound No. 28 (91.2%).

In view of the cell viabilities of the abovementioned two cancer cells and the normal fibroblast, three aspects can be discussed as follows. A first aspect points out that the compound No. 27 and the compound No. 28 have the inhibition effect on A control cell line without the cytotoxicity effect on the normal fibroblast. A second aspect points out that the compound No. 4 and the compound No. 10 have the inhibition effect on A3 cell line without the cytotoxicity effect on the normal fibroblast. A last aspect points out that the compound No. 23 and the compound No. 25 have the inhibition effect on A control cell line and A3 cell line without the cytotoxicity effect on the normal fibroblast.

Then, a cell toxicity assay of the cancer lines made by National Cancer Institute will be discussed as follows. The cell toxicity assay is performed by choosing ten compounds (existing certification numbers) from the 59 compounds disclosed in the present invention first. The cell toxicity assays of 60 cancer lines are processed to measure the inhibition effect of each compound at a fixed concentration by using in vitro DTP human cell line screen. Please refer to Table.2, the National Cancer Institute uses the compound No. 3, the compound No. 6, the compound No. 12, the compound No. 14, the compound No. 16, the compound No. 23, the compound No. 24, the compound No. 26, the compound No. 27 and the compound No. 29 as test compounds, and the results of the cell toxicity assay are shown in Table.3. According to the Table.2 and the Table.3, the compound No. 3 has the better inhibition effect on non-small cell lung cancer. The compound No. 23 has the better inhibition effect on Leukemia, non-small cell lung cancer, colorectal cancer, central nervous system cancer, ovarian cancer and kidney cancer. The compound No. 24 has the better inhibition effect on Leukemia and central nervous system cancer. The compound No. 29 has the better inhibition effect on Leukemia, non-small cell lung cancer, colorectal cancer, central nervous system cancer, ovarian cancer and kidney cancer.

TABLE 2

| No. | Structure | Chemical name, molecular weight and formula | NSC no | Concentration |
|---|---|---|---|---|
| 3 | 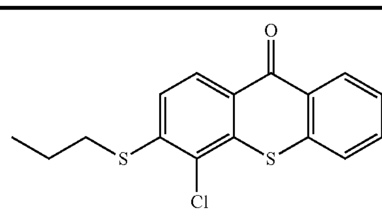 | 4-Chloro-3-(propylthio)-9H-thioxanthen-9-one<br>MW: 320.8568<br>Formula: $C_{16}H_{13}ClOS_2$ | 753739 | 1.00E−5 Molar |

TABLE 2-continued

| No. | Structure | Chemical name, molecular weight and formula | NSC no | Concentration |
|---|---|---|---|---|
| 6 | 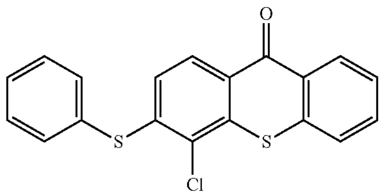 [SMILES: O=c1c2ccccc2sc2c(Cl)c(Sc3ccccc3)ccc12] | 4-Chloro-3-(phenylthio)-9H-thioxanthen-9-one<br>MW: 354.873<br>Formula: $C_{19}H_{11}ClOS_2$ | 753740 | 1.00E−5 Molar |
| 12 | 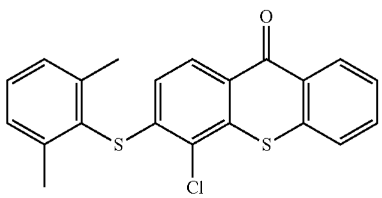 [SMILES: Cc1cccc(C)c1Sc1ccc2c(=O)c3ccccc3sc2c1Cl] | 4-Chloro-3-(2,6-dimethylphenylthio)-9H-thioxanthen-9-one<br>MW: 382.9262<br>Formula: $C_{21}H_{15}ClOS_2$ | 753741 | 1.00E−5 Molar |
| 14 | 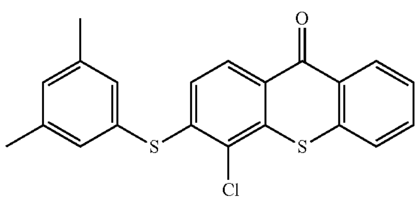 [SMILES: Cc1cc(C)cc(Sc2ccc3c(=O)c4ccccc4sc3c2Cl)c1] | 4-Chloro-3-(3,5-diemthylphenylthio)-9H-thioxanthen-9-one<br>MW: 382.9262<br>Formula: $C_{21}H_{15}ClOS_2$ | 753742 | 1.00E−5 Molar |
| 16 | 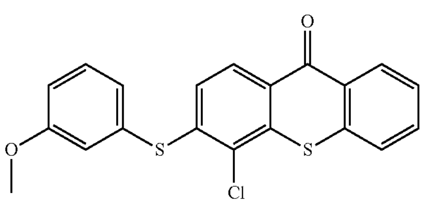 [SMILES: COc1cccc(Sc2ccc3c(=O)c4ccccc4sc3c2Cl)c1] | 4-Chloro-3-(3-methoxylphenylthio)-9H-thioxanthen-9-one<br>MW: 384.899<br>Formula: $C_{20}H_{13}ClO_2S_2$ | 753743 | 1.00E−5 Molar |
| 23 | 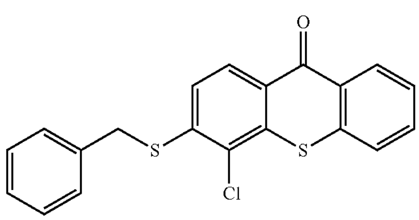 [SMILES: O=c1c2ccccc2sc2c(Cl)c(SCc3ccccc3)ccc12] | 3-(Benzylthio)-4-chloro-9H-thioxanthen-9-one<br>MW: 368.8996<br>Formula: $C_{20}H_{13}ClOS_2$ | 753744 | 1.00E−5 Molar |
| 24 | 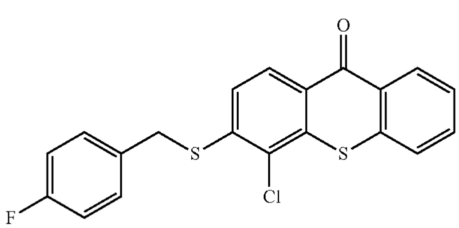 [SMILES: O=c1c2ccccc2sc2c(Cl)c(SCc3ccc(F)cc3)ccc12] | 4-Chloro-3-(4-fluorobenzylthio)-9H-thioxanthen-9-one<br>MW: 386.8901<br>Formula: $C_{20}H_{12}ClFOS_2$ | 753745 | 1.00E−5 Molar |
| 26 | 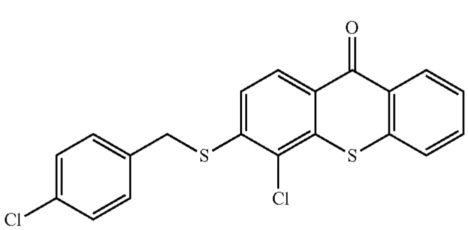 [SMILES: O=c1c2ccccc2sc2c(Cl)c(SCc3ccc(Cl)cc3)ccc12] | 4-Chloro-3-(4-chlorobenzylthio)-9H-thioxanthen-9-one<br>MW: 403.3446<br>Formula: $C_{20}H_{12}Cl_2OS_2$ | 753746 | 1.00E−5 Molar |

TABLE 2-continued

| No. | Structure | Chemical name, molecular weight and formula | NSC no | Concentration |
|---|---|---|---|---|
| 27 | 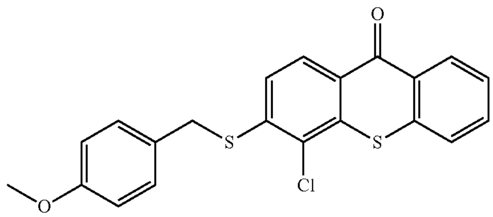 [SMILES: COc1ccc(CSc2ccc3c(=O)c4ccccc4sc3c2Cl)cc1] | 4-Chloro-3-(4-methoxybenzylthio)-9H-thioxanthen-9-one<br>MW: 398.9256<br>Formula: $C_{21}H_{15}ClO_2S_2$ | 753747 | 1.00E−5 Molar |
| 29 | 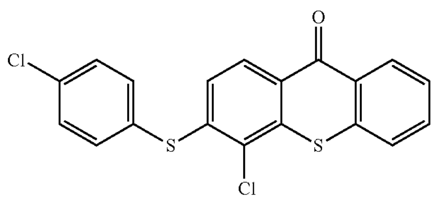 [SMILES: O=c1c2ccccc2sc2c(Cl)c(Sc3ccc(Cl)cc3)ccc12] | 4-Chloro-3-(4-chlorophenylthio)-9H-thioxanthen-9-one<br>MW: 389.3181<br>Formula: $C_{19}H_{10}Cl_2OS_2$ | 753748 | 1.00E−5 Molar |

TABLE 3

| | | Growth Percent | | | | | | | | | |
|---|---|---|---|---|---|---|---|---|---|---|---|
| Panel/Cell Line | | NO. 3 | NO. 6 | NO. 12 | NO. 14 | NO. 16 | NO. 23 | NO. 24 | NO. 26 | NO. 27 | NO. 29 |
| Leukemia | CCRF-CEM | 85.29 | 96.58 | 88.07 | N.T. | N.T. | 59.07 | 68.02 | 92.28 | 89.83 | 67.42 |
| | HL-60(TB) | 118.59 | 103.53 | 109.07 | 99.82 | 115.43 | 115.59 | 109.87 | 105.29 | 121.13 | 105.61 |
| | K562 | 94.26 | 101.65 | 97.86 | 100.94 | 97.79 | 86.95 | 90.35 | 113.64 | 114.13 | 96.64 |
| | MOLT-4 | 94.70 | 99.77 | 104.33 | 99.59 | 111.47 | 98.34 | 93.42 | 96.00 | 102.31 | 94.77 |
| | RPMI-8226 | 104.20 | 102.11 | 101.60 | 101.54 | 99.57 | 89.98 | 92.73 | 91.09 | 103.69 | 88.56 |
| | SR | 75.26 | 91.41 | 95.93 | 86.99 | 99.21 | 36.57 | 23.41 | 93.51 | 84.48 | 51.19 |
| Non-Small Cell Lung Cancer | EKVX | 96.42 | 94.90 | 103.89 | 96.66 | 96.56 | 93.46 | N.T. | 110.82 | 114.01 | 73.14 |
| | HOP-62 | 105.09 | N.T. | N.T. | N.T. | N.T. | 94.64 | 70.93 | 89.02 | 110.61 | N.T. |
| | HOP-92 | 98.11 | 76.04 | 88.79 | N.T. | N.T. | 74.60 | 76.43 | 69.89 | 78.71 | 49.52 |
| | NCI-H226 | 94.52 | 85.36 | 109.77 | 97.38 | 95.11 | 90.97 | 92.71 | 94.77 | 100.46 | 81.05 |
| | NCI-H23 | 91.47 | 84.67 | 93.96 | 92.54 | 92.69 | 97.59 | 93.31 | 96.57 | 99.92 | 83.03 |
| | NCI-H322M | 73.70 | 96.11 | 113.78 | 116.93 | 118.28 | 70.18 | 89.87 | 101.60 | 95.82 | 56.53 |
| | NCI-H460 | 59.83 | 108.87 | 110.85 | 105.72 | 108.81 | 29.14 | 60.27 | 106.85 | 107.02 | 40.25 |
| | NCI-H522 | 94.37 | 84.11 | 100.28 | 91.47 | 86.09 | 95.48 | 76.14 | 81.19 | 94.65 | 80.48 |
| Colon Cancer | COLO 205 | 92.63 | 103.82 | 110.46 | 108.10 | 113.53 | 63.36 | 86.59 | 108.87 | 99.12 | 87.02 |
| | HCC-2998 | 100.70 | 106.34 | 103.54 | 101.80 | 103.45 | 101.78 | 100.08 | 107.66 | 105.73 | 98.92 |
| | HCT-116 | 61.89 | 98.18 | 105.21 | 93.28 | 101.88 | 41.74 | 76.97 | 96.31 | 95.54 | 54.33 |
| | HCT-15 | 98.58 | 92.60 | 99.05 | 97.09 | 94.87 | 82.20 | 84.86 | 104.80 | 104.37 | 85.15 |
| | HT29 | 103.50 | 102.56 | 103.86 | 95.28 | 91.02 | 60.70 | 79.24 | 103.09 | 108.69 | 86.36 |
| | KM12 | 86.73 | 99.82 | 113.08 | 109.61 | 114.13 | 104.90 | 102.36 | 107.42 | 108.05 | 73.79 |
| | SW-620 | 87.67 | 96.96 | 105.40 | 104.39 | 106.14 | 69.53 | 78.63 | 105.00 | 106.98 | 75.00 |
| CNS Cancer | SF-268 | 80.00 | 93.39 | 98.33 | 104.92 | 104.10 | 100.29 | 95.00 | 101.57 | 101.32 | 81.14 |
| | SF-295 | 82.14 | 100.33 | 98.15 | 116.45 | 108.18 | 63.22 | N.T. | 112.42 | 107.03 | 57.86 |
| | SF-539 | 82.48 | 104.85 | 106.48 | 105.19 | 100.06 | 102.89 | 103.66 | 96.81 | 106.78 | 86.15 |
| | SNB-19 | 94.29 | 98.01 | N.T. | 108.53 | N.T. | 83.57 | 77.05 | 96.85 | 97.16 | 74.97 |
| | SNB-75 | 100.85 | 82.75 | 90.00 | 84.85 | 86.86 | 75.12 | 64.79 | 96.90 | 97.97 | 76.16 |
| | U251 | 67.20 | 94.85 | 95.70 | 95.50 | 93.76 | 38.89 | 54.73 | 86.21 | 96.42 | 47.77 |
| Melanoma | LOX IMVI | 64.69 | 96.25 | 105.37 | 96.06 | 93.53 | 62.94 | 81.78 | 97.16 | 101.59 | 63.24 |
| | MALME-3M | 92.96 | 92.44 | 100.81 | 102.39 | 94.91 | 93.38 | 93.42 | 105.22 | 107.44 | 76.90 |
| | M14 | 102.38 | 104.30 | 105.63 | 107.60 | 111.90 | 102.67 | 93.91 | 101.01 | 99.76 | 89.62 |
| | MDA-MB-435 | 80.72 | 103.22 | 107.09 | 99.38 | 100.32 | 91.01 | N.T. | 108.59 | 107.44 | 85.11 |
| | SK-MEL-2 | 114.59 | 104.71 | 108.94 | 100.30 | 97.07 | 116.81 | 108.61 | 90.37 | 104.94 | 105.36 |
| | SK-MEL-28 | 104.13 | 113.07 | 110.00 | 117.96 | 109.16 | 119.10 | 107.78 | 114.10 | 118.75 | 114.93 |
| | SK-MEL-5 | 98.20 | 95.50 | 104.77 | 104.23 | 96.73 | 99.73 | 95.97 | 101.76 | 101.55 | 88.35 |
| | UACC-257 | 98.85 | 102.79 | 92.09 | 89.26 | 89.21 | 109.84 | 103.43 | 92.94 | 100.47 | 99.23 |
| | UACC-62 | 84.56 | 79.70 | N.T. | 96.19 | N.T. | 90.92 | 85.61 | 92.54 | 91.61 | 82.23 |
| Ovarian Cancer | IGROV1 | 91.28 | 91.62 | 98.49 | 100.06 | 108.37 | 56.63 | 79.84 | 104.47 | 108.76 | 53.39 |
| | OVCAR-3 | 90.35 | 108.01 | 113.05 | 121.13 | 113.99 | 76.97 | 105.27 | 130.11 | 125.16 | 90.37 |
| | OVCAR-4 | 73.74 | 99.56 | 107.51 | 101.64 | 99.88 | 6.10 | 39.21 | 107.67 | 104.27 | 31.58 |
| | OVCAR-5 | 94.79 | 104.51 | 96.86 | 98.39 | 94.14 | 94.34 | 108.14 | 102.23 | 103.70 | 107.36 |
| | OVCAR-8 | 83.50 | 94.68 | 96.86 | 97.95 | 94.29 | 82.11 | 85.39 | 86.47 | 95.58 | 64.49 |
| | NCI/ADR-RES | 93.97 | 96.88 | 105.14 | 101.13 | 102.83 | 90.62 | 92.71 | 100.89 | 106.73 | 81.27 |
| | SK-OV-3 | 104.52 | 96.13 | 111.32 | 103.14 | 104.91 | 94.39 | 90.11 | 97.10 | 107.96 | 73.85 |
| Renal | 786-0 | 101.51 | 111.45 | 108.98 | 110.62 | 107.97 | 78.53 | 91.67 | 106.48 | 100.89 | 84.66 |

TABLE 3-continued

| | | Growth Percent | | | | | | | | | |
|---|---|---|---|---|---|---|---|---|---|---|---|
| Panel/Cell Line | | NO. 3 | NO. 6 | NO. 12 | NO. 14 | NO. 16 | NO. 23 | NO. 24 | NO. 26 | NO. 27 | NO. 29 |
| Cancer | ACHN | 74.17 | 94.03 | 103.68 | 98.35 | 103.08 | 26.15 | 60.81 | 91.82 | 104.71 | 39.55 |
| | CAKI-1 | 78.97 | 84.00 | 89.35 | 90.10 | 101.23 | 54.75 | N.T. | 98.76 | 102.18 | 48.21 |
| | RXF 393 | 106.97 | 110.95 | N.T. | 114.27 | 112.67 | 106.84 | 92.20 | 109.38 | 117.83 | 97.81 |
| | SN12C | 85.72 | 87.55 | N.T. | 101.79 | N.T. | 79.25 | 84.46 | 94.51 | 94.49 | 70.19 |
| | TK-10 | 103.80 | 97.85 | 99.22 | 103.30 | 95.23 | 95.49 | 83.61 | 100.13 | 105.39 | 88.86 |
| | UO-31 | 99.45 | 73.68 | 87.03 | 87.22 | 98.31 | 66.76 | 95.13 | 89.66 | 102.53 | 69.61 |
| Prostate | PC-3 | 94.80 | 90.81 | 98.56 | 97.92 | 98.58 | 83.92 | 86.19 | 93.28 | 93.39 | 77.10 |
| Cancer | DU145 | 91.93 | 108.05 | 109.56 | 118.42 | 115.18 | 107.70 | 103.70 | 108.56 | 114.70 | 108.68 |
| Breast | MCF7 | 97.13 | 82.14 | 94.01 | 94.94 | 88.94 | 89.62 | 89.93 | 94.48 | 101.77 | 83.90 |
| Cancer | MDA-MB-231/ATCC | 85.71 | 93.94 | 108.12 | 106.25 | N.T. | 71.98 | 81.64 | 95.00 | 96.93 | 77.55 |
| | HS 578-T | 94.80 | 119.59 | 107.64 | 103.67 | 103.73 | 91.28 | 67.70 | 108.61 | 124.03 | 102.79 |
| | BT-549 | 93.64 | 107.30 | 105.28 | 105.50 | 112.48 | 84.98 | 88.80 | 94.67 | 93.21 | 87.92 |
| | T-47D | 98.14 | 87.90 | 97.56 | 100.87 | 92.09 | 82.55 | 81.88 | 87.73 | 88.81 | 85.63 |
| | MDA-MB-468 | 91.53 | 82.54 | 113.20 | 110.63 | 104.49 | 73.81 | 92.16 | 96.96 | 102.80 | 87.73 |
| Mean | | 91.31 | 96.75 | 102.52 | 101.73 | 101.65 | 81.22 | 85.42 | 99.47 | 103.13 | 78.44 |
| Delta | | 31.48 | 23.07 | 15.49 | 16.88 | 15.56 | 66.12 | 62.01 | 29.58 | 24.42 | 46.86 |
| Range | | 58.76 | 45.91 | 26.75 | 36.28 | 32.19 | 104.00 | 86.46 | 60.22 | 46.45 | 83.35 |

The present invention provides a series of thioxanthone ring system derivative compound, and further provides a method for manufacturing the same and a pharmaceutical composition comprising the same. The thioxanthone ring system derivative compound is represented by a formula (I):

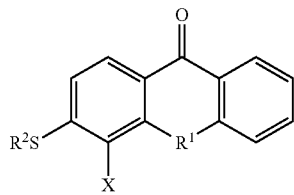

Wherein 3-position combines various sulfur substituent, and the pharmaceutical composition contained the thioxanthone ring system derivative compound effetely inhibit telomerase activity (that is, tumor growth).

According to the results of the pharmacological assay, the inhibition effect of the thioxanthone ring system derivative compound, which the sulfur substituent combined at 3-position of the thioxanthone ring system derivative compound has a benzene ring, will be better. Furthermore, the interval; between sulfur and the benzene ring also effect the inhibition effect.

Although the present invention has been described in considerable detail with reference to certain preferred embodiments thereof, the disclosure is not for limiting the scope of the invention. Persons having ordinary skill in the art may make various modifications and changes without departing from the scope and spirit of the invention. Therefore, the scope of the appended claims should not be limited to the description of the preferred embodiments described above.

What is claimed is:

1. A thioxanthone ring system derivative compound is represented by a formula (I):

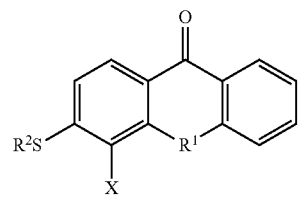

wherein X is a substituent being one selected from a group consisting of halogens, wherein $R^1$ is a substituent being one selected from a group consisting of sulfur and sulfur dioxide, wherein $R^2$ is a substituent being one selected from a group consisting of $C_1$~$C_{10}$ alkyl group, $C_3$~$C_{10}$ branched alkyl group, $C_3$~$C_{10}$ cyclic alkyl group, phenyl group, phenyl alkyl group, and wherein hydrogen of phenyl group being partially substituted by halogens, alkoxyl group, $C_1$~$C_{10}$ alkyl group, nitro group or amine group.

2. The thioxanthone ring system derivative compound according to claim 1, wherein $R^2$ is $C_1$~$C_{10}$ alkyl group, and one selected from a group consisting of a methyl group, an ethyl group, a propyl group, a butyl group, a pentyl group, a hexyl group, a heptyl group, an octyl group, an nonyl group and a decyl group.

3. The thioxanthone ring system derivative compound according to claim 2, wherein $R^2$ is the ethyl group or the propyl group.

4. The thioxanthone ring system derivative compound according to claim 1, wherein $R^2$ is $C_3$~$C_{10}$ branched alkyl group, and one selected from a group consisting of an isobutyl group, an isopentyl group, 2-methylbutyl group, 2-methylpentyl group, 3-methylpentyl group, 2-methylhexyl group, 3-methylhexyl group, 2-ethylpentyl group, 2-methylheptyl group, 3-methylheptyl group, 4-methylheptyl group, 3-ethylpentyl group, 2-methyloctyl group, 3-methyloctyl group, 4-methyloctyl group, 3-ethylheptyl group, 4-ethylheptyl group, 2-methylnonyl group, 3-methylnonyl group, 4-methylnonyl group, 5-methylnonyl group, 3-ethyloctyl group, 4-ethyloctyl group.

5. The thioxanthone ring system derivative compound according to claim 4, wherein $R^2$ is the isobutyl group.

6. The thioxanthone ring system derivative compound according to claim 1, wherein $R^2$ is $C_3$~$C_{10}$ cyclic alkyl group, and one selected from a group consisting of a cyclopropyl group, a cyclobutyl group, a cyclopentyl group, a cyclohexyl group, a cycloheptyl group, a cyclooctyl group, a cyclononyl group, a cyclodecyl group.

7. The thioxanthone ring system derivative compound according to claim 6, wherein $R^2$ is the cyclopentyl group.

8. The thioxanthone ring system derivative compound according to claim 1, wherein $R^2$ is the phenyl group or the phenyl alkyl group, and one selected from a group consisting of a nitrophenyl group, an alkoxyphenyl group, an aminophenyl group, a methylphenyl group, a chlorophenyl group, a bromophenyl group, an isopropylphenyl group, an ethylphenyl group.

9. The thioxanthone ring system derivative compound according to claim 8, wherein $R^2$ is a 4-nitrophenyl group, a 2-methoxyphenyl group, a 3-methoxyphenyl group, a 4-methoxyphenyl group, a 2-ethoxyphenyl group, a 2-aminophenyl group, a 3-aminophenyl group, a 2-methylphenyl group, a 3-methylphenyl group, a 4-methylphenyl group, a 3-chlorophenyl group, a 4-chlorophenyl group, a 2,3-dichlorophenyl group, a 4-bromophenyl group, a 2,4-dimethylphenyl group, a 2,5-dimethylphenyl group, a 2,6-dimethylphenyl group, a 3,4-dimethylphenyl group, a 3,5-dimethylphenyl group, a 2-isopropylphenyl group, a 4-isopropyl group or a 2-ethylphenyl group.

10. The thioxanthone ring system derivative compound according to claim 1, wherein $R^2$ is a 2-chlorophenylmethyl group, a 4-fluorophenylmethyl group, a 4-bromophenylmethyl group, a 4-chlorophenylmethyl group, a 4-methoxyphenylmethyl group, a 2,4,6-trimethylphenyl group or a 4-isopropylphenylmethyl group.

11. The thioxanthone ring system derivative compound according to claim 1, wherein the halogen is one selected from a group consisting of a fluorine, a chlorine, a bromine and an iodine.

12. A pharmaceutical composition for inhibiting tumor growth, comprising a thioxanthone ring system derivative compound with an effective amount and a pharmaceutically acceptable excipient, wherein the thioxanthone ring system derivative compound being represented by a formula (I) according to claim 1.

13. The pharmaceutical composition according to claim 12, wherein the tumor is a solid tumor or a non-solid tumor.

14. The pharmaceutical composition according to claim 13, wherein a cancer having the solid tumor is selected from lung cancer, colorectal cancer, central nervous system cancer, melanoma, ovarian cancer, prostate cancer, kidney cancer, and breast cancer.

15. The pharmaceutical composition according to claim 13, wherein a cancer having the non-solid tumor is Leukemia.

* * * * *